United States Patent
Nishikori

(10) Patent No.: US 11,281,100 B2
(45) Date of Patent: Mar. 22, 2022

(54) RADIATION-SENSITIVE RESIN COMPOSITION, ONIUM SALT COMPOUND AND METHOD FOR FORMING RESIST PATTERN

(71) Applicant: JSR CORPORATION, Tokyo (JP)

(72) Inventor: Katsuaki Nishikori, Tokyo (JP)

(73) Assignee: JSR CORPORATION, Tokyo (JP)

( * ) Notice: Subject to any disclaimer, the term of this patent is extended or adjusted under 35 U.S.C. 154(b) by 278 days.

(21) Appl. No.: 16/424,986

(22) Filed: May 29, 2019

(65) Prior Publication Data

US 2019/0285983 A1    Sep. 19, 2019

Related U.S. Application Data

(63) Continuation-in-part of application No. PCT/JP2017/042837, filed on Nov. 29, 2017.

(30) Foreign Application Priority Data

Dec. 1, 2016    (JP) .............................. JP2016-233907

(51) Int. Cl.
| | | |
|---|---|---|
| *G03F 7/004* | (2006.01) | |
| *C07C 309/17* | (2006.01) | |
| *C07C 381/12* | (2006.01) | |
| *C07D 307/12* | (2006.01) | |
| *C07D 307/33* | (2006.01) | |
| *C07D 317/38* | (2006.01) | |
| *C07D 333/46* | (2006.01) | |
| *G03F 7/038* | (2006.01) | |
| *G03F 7/039* | (2006.01) | |
| *C09K 3/00* | (2006.01) | |
| *G03F 7/20* | (2006.01) | |
| *G03F 7/16* | (2006.01) | |
| *G03F 7/32* | (2006.01) | |
| *G03F 7/38* | (2006.01) | |

(52) U.S. Cl.
CPC .......... *G03F 7/0045* (2013.01); *C07C 309/17* (2013.01); *C07C 381/12* (2013.01); *C07D 307/12* (2013.01); *C07D 307/33* (2013.01); *C07D 317/38* (2013.01); *C07D 333/46* (2013.01); *C09K 3/00* (2013.01); *G03F 7/004* (2013.01); *G03F 7/038* (2013.01); *G03F 7/039* (2013.01); *G03F 7/20* (2013.01); *C07C 2601/14* (2017.05); *C07C 2602/42* (2017.05); *C07C 2603/18* (2017.05); *C07C 2603/74* (2017.05); *G03F 7/162* (2013.01); *G03F 7/168* (2013.01); *G03F 7/2006* (2013.01); *G03F 7/2041* (2013.01); *G03F 7/322* (2013.01); *G03F 7/38* (2013.01)

(58) Field of Classification Search
CPC .... C07C 381/12; C07C 309/12; G03F 7/0045
See application file for complete search history.

(56) References Cited

U.S. PATENT DOCUMENTS

| | | | | |
|---|---|---|---|---|
| 9,200,098 | B2 * | 12/2015 | Maruyama | G03F 7/0045 |
| 9,304,393 | B2 * | 4/2016 | Nakahara | G03F 7/0046 |
| 2015/0338736 | A1 | 11/2015 | Kawabata et al. | |

FOREIGN PATENT DOCUMENTS

| | | |
|---|---|---|
| JP | H10-10715 A | 1/1998 |
| JP | H10-10715 A | 1/1998 |
| JP | 2014-126767 A | 7/2014 |

OTHER PUBLICATIONS

Combined Taiwanese Office Action and Search Report dated Dec. 14, 2020 in Taiwanese Patent Application No. 106141929 (with English translation), 8 pages.
English translation of the International Preliminary Report on Patentability and Written Opinion dated Jun. 13, 2019 in PCT/JP2017/042837.
Office Action dated Aug. 31, 2021 in corresponding Japanese Patent Application No. 2018-554200 (with English Translation), 4 pages.
International Search Report dated Jan. 23, 2018 in PCT/JP2017/042837 (with English translation).
Office Action dated Jan. 4, 2022 in corresponding Japanese Patent Application No. 2018-554200, filed Nov. 29, 2017 (with English-language Translation), 4 pages.

* cited by examiner

*Primary Examiner* — Amanda C. Walke
(74) *Attorney, Agent, or Firm* — Oblon, McClelland, Maier & Neustadt, L.L.P.

(57) ABSTRACT

A radiation-sensitive resin composition includes a resin including a structural unit having an acid-dissociable group, an onium salt compound represented by formula (1), and a solvent.
$R^1$ is a hydrogen atom or a monovalent group provided that the monovalent group is not a fluoro group or a monovalent organic group containing a fluorine atom. $X^1$ and $X^2$ are each independently a single bond, —O—, —S— or —NR'— wherein R' is a hydrogen atom or a monovalent hydrocarbon group. In a case where $X^1$ is —NR'—, $R^2$ is a monovalent organic group or a hydrogen atom. In a case where $X^2$ is —NR'—, $R^3$ is a monovalent organic group or a hydrogen atom. In a case where neither $X^1$ nor $X^2$ is —NR'—, $R^2$ and $R^3$ are each independently a monovalent organic group.

(1)

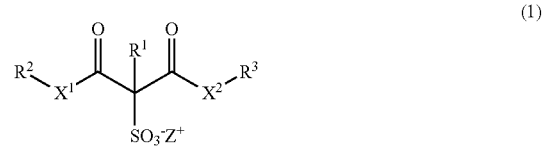

20 Claims, No Drawings

RADIATION-SENSITIVE RESIN COMPOSITION, ONIUM SALT COMPOUND AND METHOD FOR FORMING RESIST PATTERN

CROSS-REFERENCE TO RELATED APPLICATIONS

The present application is a continuation-in-part application of International Application No. PCT/JP2017/042837, filed Nov. 29, 2017, which claims priority to Japanese Patent Application No. 2016-233907, filed Dec. 1, 2016. The contents of these applications are incorporated herein by reference in their entirety.

BACKGROUND OF THE INVENTION

Field of the Invention

The present invention relates to a radiation-sensitive resin composition, an onium salt compound and a method for forming a resist pattern.

Description of the Related Art

A photolithography technology using a resist composition has been used for the fine circuit formation in a semiconductor device. As the representative procedure, for example, a resist pattern is formed on a substrate by generating an acid by irradiating the coating of the resist composition with a radioactive ray through a mask pattern, and then reacting in the presence of the acid as a catalyst to generate the difference of solubility of a resin into an alkaline or organic developer between an exposed part and a non-exposed part.

In the photolithography technology, the micronization of the pattern is promoted by using a short wave length radioactive ray such as ArF excimer laser, and by using immersion exposure method (liquid immersion lithography) in which the exposure is carried out in a liquid medium filled in the space between a lens of an exposing apparatus and a resist film. As a next generation technology, a lithography using a short wave length such as an electron beam, X ray and EUV (extreme ultraviolet ray) has been studied.

With progress of the exposing technology, studies of a photoacid generator and the like, a major ingredient of the resist composition, are attempted for the purpose of improving the sensitivity and resolution of the resist composition. As the resist composition having a pattern resolution from micron size to submicron size, proposed is a photosensitive composition including a hydroxystyrene-based polymer having high plasma etching resistance and a photoacid generator having a carbon atom connected to a sulfonate group as a secondary carbon or a tertiary carbon (JP-A-10-10715). However, as wavelength shortening of radiation for exposure progresses, since the absorption by the aromatic structure of the hydroxystyrene-based polymer becomes too strong, it is difficult to form a desired fine shape of pattern.

Therefore, there has been used a resin having an alicyclic structure having weak absorption as a protecting group in place of the hydroxystyrene-based polymer. However, the photoacid generator used in combination of the hydroxystyrene-based polymer have no sufficient acid intensity in order to proceed the deprotection of the resin having an alicyclic structure. Therefore, an acid generator in which a carbon proximal to the sulfonate group is perfluorinated is implemented, as a photoacid generator resulting in an acid having a sufficient acid intensity for the deprotection. Meanwhile, from the viewpoint of a rise in awareness of environmental issues in recent years, suggested is a low-degree fluorinated sulfonic acid salt having decreased fluorine content in order to reduce loads onto the environment (JP-A-2014-126767).

SUMMARY OF THE INVENTION

According to an aspect of the present invention, a radiation-sensitive resin composition includes a resin including a structural unit having an acid-dissociable group, an onium salt compound represented by formula (1), and a solvent.

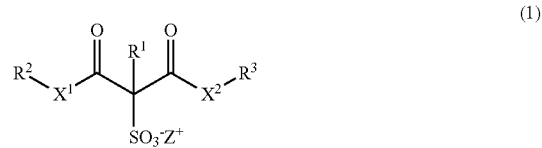

(1)

$R^1$ is a hydrogen atom or a monovalent group provided that the monovalent group represented by $R^1$ is not a fluoro group or a monovalent organic group containing a fluorine atom. $X^1$ and $X^2$ are each independently a single bond, —O—, —S— or —NR'— wherein R' is a hydrogen atom or a monovalent hydrocarbon group, provided that when two R's are present, the two R's are the same or different. In a case where $X^1$ is —NR'—, $R^2$ is a monovalent organic group or a hydrogen atom. In a case where $X^2$ is —NR'—, $R^3$ is a monovalent organic group or a hydrogen atom. In a case where neither $X^1$ nor $X^2$ is —NR'—, $R^2$ and $R^3$ are each independently a monovalent organic group. Optionally, in a case where $X^1$ is —NR'—, $R^2$ is linked to R' in $X^1$ to form a cyclic structure. Optionally, in a case where $X^2$ is —NR'—, $R^3$ is linked to R' in $X^2$ to form a cyclic structure. $R^2$ and $R^3$ are optionally linked with each other to form a cyclic structure.

According to another aspect of the present invention, an onium salt compound is represented by formula (1).

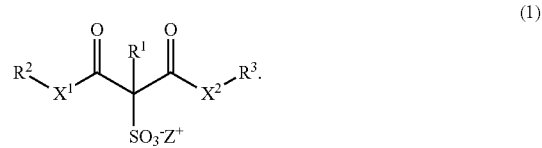

(1)

$R^1$ is a hydrogen atom or a monovalent group provided that the monovalent group represented by $R^1$ is not a fluoro group or a monovalent organic group containing a fluorine atom. $X^1$ and $X^2$ are each independently a single bond, —O—, —S— or —NR'— wherein R' is a hydrogen atom or a monovalent hydrocarbon group, provided that when two R's are present, the two R's are the same or different. In a case where $X^1$ is —NR'—, $R^2$ is a monovalent organic group or a hydrogen atom. In a case where $X^2$ is —NR'—, $R^3$ is a monovalent organic group or a hydrogen atom. In a case where neither $X^1$ nor $X^2$ is —NR'—, $R^2$ and $R^3$ are each independently a monovalent organic group. Optionally, in a case where $X^1$ is —NR'—, $R^2$ is linked to R' in $X^1$ to form a cyclic structure. Optionally, in a case where $X^2$ is —NR'—, $R^3$ is linked to R' in $X^2$ to form a cyclic structure. $R^2$ and $R^3$ are optionally linked with each other to form a cyclic structure.

According to further aspect of the present invention, a method for forming a resist pattern, includes applying the radiation-sensitive resin composition on a substrate to form a resist film. The resist film is exposed. The resist film is developed after the exposing of the resist film.

DETAILED DESCRIPTION OF THE
PREFERRED EMBODIMENTS

The embodiment of the present invention relates to a radiation-sensitive resin composition including:
a resin including a structural unit having an acid-dissociable group;
an onium salt compound represented by a formula (1); and
a solvent:

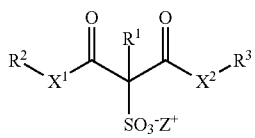

(1)

wherein:
$Z^+$ is a monovalent onium cation;
$R^1$ is a hydrogen atom or a monovalent group provided that the monovalent group represented by $R^1$ is not a fluoro group or a monovalent organic group containing a fluorine atom;
$X^1$ and $X^2$ are each independently a single bond, —O—, —S— or —NR'— wherein R' is a hydrogen atom or a monovalent hydrocarbon group, provided that when two R's are present, the two R's are the same or different; and
in a case where $X^1$ is —NR'—, $R^2$ is a monovalent organic group or a hydrogen atom,
in a case where $X^2$ is —NR'—, $R^3$ is a monovalent organic group or a hydrogen atom,
in a case where neither $X^1$ nor $X^2$ is —NR'—, $R^2$ and $R^3$ are each independently a monovalent organic group,
optionally, in a case where $X^1$ is —NR'—, $R^2$ is linked to R' in $X^1$ to form a cyclic structure,
optionally, in a case where $X^2$ is —NR'—, $R^3$ is linked to R' in $X^2$ to form a cyclic structure, and
$R^2$ and $R^3$ are optionally linked with each other to form a cyclic structure.

The onium salt compound represented by the formula (1) can make the strength of the acid high even in the case of not introducing a fluorine atom or fluorinated substituent (such as a perfluoroalkyl group) which is introduced into any conventional photo acid generator and which is on a carbon atom (in particular, an α-position carbon atom or a β-position carbon atom) near the sulfonate group. Without wishing to be bound by any theory, a reason therefor is presumed as follows: two electrophilic carbonyl groups are bonded to the carbon atom (α-position carbon atom) to which the sulfonate group is bonded; thus, an electron in the sulfonate group is attracted toward the α-position carbon atom of this compound so that the sulfonate ion is stabilized to contribute to an improvement of the compound in acid strength (a lowering thereof in pKa). This radiation-sensitive resin composition makes it possible to exhibit a sufficient acid strength while the composition contributes greatly to a lowering of the compound in fluorination degree. Moreover, the radiation-sensitive resin composition makes it possible to make various resist performances at a good level, examples of these performances including LWR performance, resolution, sectional-shape rectangle-property, focal depth, MEEF performance and film-shrinkage-restraining performance. A reason therefor is unclear; however, this good level is presumed on the basis of the following complex factors: a sufficient acid strength as described above; the fact that hydrogen bonds are formed between oxygens in the two carbonyl groups, which are near to each other at the β-positions, and hydrogen in the resin, so as to produce an anchor effect to control the diffusion length of the acid appropriately; and the fact that the onium salt compound is restrained from being unevenly present in the resist film by a decrease of fluorine atoms in quantity or number.

It is preferred that at least one of $R^2$ and $R^3$ has a cyclic structure. When the onium salt compound has the cyclic structure, the diffusion length of the resultant acid can be set into an appropriate range so that various resist performances can be improved.

Specifically, at least one of $R^2$ and $R^3$ may be a group having an alicyclic hydrocarbon group having a carbon atom number of 3 to 20. Moreover, at least one of $R^2$ and $R^3$ may be a group including at least one structure selected from the group consisting of a lactone structure, a cyclic carbonate structure, a cyclic acetal structure, a cyclic ether structure and a sultone structure. Alternatively, at least one of $R^2$ and $R^3$ may be a group having an aromatic hydrocarbon group having a carbon atom number of 6 to 20. In the case of using, as the cyclic structure of the onium salt compound, one of these groups or a combination of two or more thereof, the diffusion length of the acid obtained from this onium salt compound is appropriately controllable to improve various resist performances effectively.

It is preferred that neither $R^2$ nor $R^3$ has a cyclic structure; and
at least one of $R^2$ and $R^3$ is a chain hydrocarbon group which has a carbon atom number of 1 to 20 and is optionally substituted with at least one substituent selected from the group consisting of a halogen atom and a polar group.

Also when the onium salt compound makes use of a predetermined straight chain hydrocarbon group having at least one of a halogen atom and a polar group (these may be collectively referred to as a "polar structure") instead of the cyclic structure, the various resist performances can be improved. One reason therefor is presumed as follows: hydrogen bonds are induced between the resultant acid and the resin so that the diffusion length of the acid is controlled.

It is preferred that the onium cation is a sulfonium cation or an iodonium cation. These onium cations are each easily decomposed by radioactive ray irradiation, so that the generation efficiency of the acid can be heightened.

The radiation-sensitive resin composition is suitable for resist-pattern formation in which exposure is performed with a radioactive ray having a wavelength of 50 nm or less. Also with an ArF excimer laser (wavelength: 193 nm), the onium salt compound has a sufficient de-protection effect to a resin having an alicyclic structure. The de-protection can be further promoted by radiation exposure using a radioactive ray having a wavelength of 50 nm or less, such as an EUV (extreme ultraviolet ray; wavelength: 13.5 nm), and various resist performances (i.e., high resolution, good rectangle-property of their cross sections, good line width roughness (LWR) performance which shows a variation of the patterns in line width, a high focal depth and good mask error factor (MEEF) performance, and a good performance such that when a resist film is subjected to post exposure baking (PEB), a shrinkage of this film is small) can be promoted in next-generation exposure technology.

The embodiment of the present invention also relates to an onium salt compound represented by a formula (1):

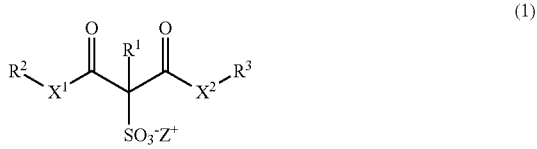

wherein:

$Z^+$ is a monovalent onium cation;

$R^1$ is a hydrogen atom or a monovalent group provided that the monovalent group represented by $R^1$ is not a fluoro group or a monovalent organic group containing a fluorine atom;

$X^1$ and $X^2$ are each independently a single bond, —O—, —S— or —NR'— wherein R' is a hydrogen atom or a monovalent hydrocarbon group, provided that when two R's are present, the two R's are the same or different; and in a case where $X^1$ is —NR'—, $R^2$ is a monovalent organic group or a hydrogen atom, in a case where $X^2$ is —NR'—, $R^3$ is a monovalent organic group or a hydrogen atom, in a case where neither $X^1$ nor $X^2$ is —NR'—, $R^2$ and $R^3$ are each independently a monovalent organic group, optionally, in a case where $X^1$ is —NR'—, $R^2$ is linked to R' in $X^1$ to form a cyclic structure, optionally, in a case where $X^2$ is —NR'—, $R^3$ is linked to R' in $X^2$ to form a cyclic structure, and $R^2$ and $R^3$ are optionally linked with each other to form a cyclic structure.

The onium salt compound makes it possible to decrease loads onto the environment by a lowering in the degree of fluorination, and further to form a resist pattern satisfying various resist performances also in next-generation exposure technology.

The embodiment of the present invention further relates to a method for forming a resist pattern, including applying the radiation-sensitive resin composition on a substrate to form a resist film;

exposing the resist film; and developing the resist film after the exposing of the resist film.

This forming method makes it possible to promote a lowering in the degree of fluorination to form a high-quality resist pattern through a process small in load onto the environment by using the radiation-sensitive resin composition.

<Radiation-Sensitive Resin Composition>

The radiation-sensitive resin composition according to the present embodiment (hereinafter, also referred simply as a "composition") includes a resin, an onium salt compound, and a solvent. The composition may also include an optional ingredient as long as the effect of the present invention is not impaired.

(Resin)

The resin is an aggregation of polymers, each polymer including a structural unit having an acid-dissociable group (hereinafter, also referred as a "structural unit (I)"). (Hereinafter, the resin is also referred as a "base resin".) The "acid-dissociable group" refers to a substituent group with which a hydrogen atom in a group such as a carboxy group, a phenolic hydroxide group is substituted, and the acid-dissociable group is dissociated by an acid. The radiation-sensitive resin composition provides an improved patternability because of the resin including the structural unit (I).

Preferably, the base resin includes a structural unit (II) in addition to the structural unit (I), the structural unit (II) including at least one selected from the group consisting of a lactone structure, a cyclic carbonate structure and a sultone structure as described below. The base resin may include any other structural unit other than the structural unit (I) and the structural unit (II). Each of the structural units will now be described.

[Structural Unit (I)]

The structural unit (I) is a structural unit containing an acid-dissociable group. The structural unit (I) is not particularly limited as far as this unit contains an acid-dissociable group. This unit is, for example, a structural unit derived from an acid-dissociable ester group of an unsaturated carboxylic acid, a structural unit derived from hydroxystyrene, or a structural unit having an acetal bond. From the viewpoint of an improvement of the radiation-sensitive resin composition in pattern-forming performance, a structural unit represented by a formula (2) illustrated below (hereinafter the unit may be referred to also as the "structural unit (I-1)") is preferred.

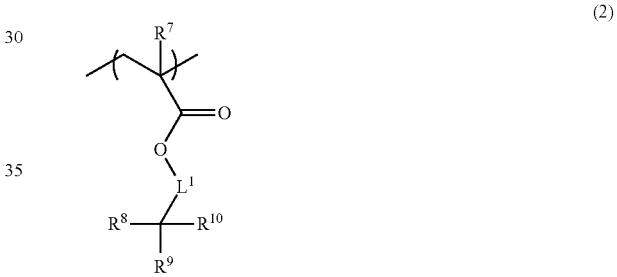

In the above formula (2), $R^7$ is a hydrogen atom, a fluorine atom, a methyl group, or a trifluoromethyl group; $R^8$ is a hydrogen atom, or a monovalent hydrocarbon group having a carbon number of 1 to 20; $R^9$ and $R^{10}$ are each independently a monovalent chain hydrocarbon group having a carbon number of 1 to 10, or a monovalent alicyclic hydrocarbon group having a carbon number of 3 to 20, or represent a divalent alicyclic group having a carbon number of 3 to 20, which is obtained by combining $R^9$ and $R^{10}$ with the carbon atom to which they are bound; L represents a single bond, or a divalent linking group.

As $R^7$ described above, in terms of the copolymerizability of monomers resulting in the structural unit (I), a hydrogen atom or a methyl group is preferred. A methyl group is more preferred.

Examples of the monovalent hydrocarbon group having a carbon number of 1 to 20 represented by $R^8$ as described above include a chain hydrocarbon group having a carbon number of 1 to 10, a monovalent alicyclic hydrocarbon group having a carbon number of 3 to 20, and a monovalent aromatic hydrocarbon group having a carbon number of 6 to 20.

Examples of the chain hydrocarbon group having 1 to 10 carbon atoms, which is represented by each of $R^8$ to $R^{10}$, include:

alkyl groups such as methyl, ethyl, n-propyl, i-propyl, n-butyl, 2-methylpropyl, 1-methylpropyl, and t-butyl groups;

alkenyl groups such as ethenyl, propenyl, and butenyl groups; and alkynyl groups such as ethynyl, propynyl, and butynyl groups.

Examples of the alicyclic hydrocarbon group having 3 to 20 carbon atoms, which is represented by each of $R^8$ to $R^{10}$, include:

monocyclic cycloalkyl groups such as cyclopropyl, cyclobutyl, cyclopentyl, and cyclohexyl groups;

polycyclic cycloalkyl groups such as norbornyl, adamantyl, tricyclodecyl, and tetracyclododecyl groups;

cycloalkenyl groups such as cyclopropenyl, cyclobutenyl, cyclopentenyl, and cyclohexenyl groups; and polycyclic cycloalkenyl groups such as norbornenyl, tricyclodecenyl, and tetracyclododecenyl groups.

Examples of the monovalent aromatic hydrocarbon group having a carbon number of 6 to 20 represented by $R^8$ as described above include an aryl group including a phenyl group, a tolyl group, a xylyl group, a naphthyl group, and an anthryl group; and an aralkyl group including a benzyl group, a phenethyl group, and a naphthyl methyl group.

Preferred examples of $R^8$ include a chain hydrocarbon group having a carbon number of 1 to 10, and a monovalent alicyclic hydrocarbon group having a carbon number of 3 to 20.

The divalent alicyclic group having a carbon number of 3 to 20, which is obtained by combining a combination of the chain hydrocarbon group or the alicyclic hydrocarbon group represented by $R^9$ and $R^{10}$ with the carbon atom to which they are bound, is not particularly limited as long as the group is a group obtained by removing two hydrogen atoms from the same carbon atom of a monocyclic or polycyclic alicyclic hydrocarbon carbocyclic ring having the same number of carbon atoms as described above. The group may be a monocyclic hydrocarbon group or a polycyclic hydrocarbon group. The polycyclic hydrocarbon group may be a bridged alicyclic hydrocarbon group or a non-bridged alicyclic hydrocarbon group, and may be a saturated hydrocarbon group or an unsaturated hydrocarbon group. The bridged alicyclic hydrocarbon group denotes an alicyclic hydrocarbon group having a structure of bridging two or more out of carbon atoms constituting an alicyclic ring with one or more carbon atoms, and the non-bridged alicyclic hydrocarbon group denotes an alicyclic hydrocarbon group having a structure of bridging carbon atoms constituting an alicyclic ring with single bonds, respectively.

Examples of the monocyclic alicyclic hydrocarbon group include:

saturated hydrocarbon groups such as cyclopropanediyl, cyclobutanediyl, cyclopentanediyl, cyclohexanediyl, cycloheptanediyl, cyclooctanediyl, cyclodecanediyl, and cyclododecanediyl groups; and unsaturated hydrocarbon groups such as cyclopropenediyl, cyclobutenediyl, cyclopentenediyl, cyclohexenediyl, cycloheptenediyl, cyclooctenediyl, and cyclodecenediyl groups.

Examples of the polycyclic alicyclic hydrocarbon group include:

non-bridged alicyclic saturated hydrocarbon groups such as bicyclo[1.1.0]butane-2,2-diyl, bicyclo[2.1.0]pentane-2,2-diyl, and bicyclo[2.2.0]hexane-2,2-diyl groups;

bridged alicyclic saturated hydrocarbon groups such as bicyclo[2.2.1]heptane-2,2-diyl (norbornane-2,2-diyl), bicyclo[2.2.2]octane-2,2-diyl, and tricyclo[3.3.1.1$^{3,7}$]decane-2,2-diyl (adamanthane-2,2-diyl) groups;

non-bridged unsaturated hydrocarbon groups such as bicyclo[2.1.0]pentene-2,2-diyl, and bicyclo[2.2.0]hexene-2,2-diyl groups; and bridged unsaturated hydrocarbon groups such as bicyclo[2.2.1]heptene-2,2-diyl, bicyclo[2.2.1]heptadiene-2,2-diyl, bicyclo[2.2.2]octene-2,2-diyl, bicyclo[2.2.2]octadiene-2,2-diyl, and bicyclo[2.2.2]octatriene-2,2-diyl groups.

Among these examples, monocyclic and polycyclic alicyclic saturated hydrocarbon groups are preferred.

Examples of the divalent linking group represented by $L^1$ include alkanediyl, cycloalkanediyl, alkenediyl and arenediyl groups, and *—$R^{LA}$O— and *—$R^{LA}$COO— wherein each * represents a bonding hand of one of these two groups on the oxygen side thereof. Hydrogen atoms which these groups have may be partially or wholly substituted with, for example, one or more halogen atoms such as fluorine or chlorine atoms, or one or more cyano groups.

Examples of the alkanediyl group include methanediyl, ethanediyl, propanediyl, butanediyl, hexanediyl, and octanediyl groups. The alkanediyl group is preferably an alkanediyl group having a carbon atom number of 1 to 8.

Examples of the cycloalkanediyl group include a monocyclic cycloalkanediyl group including a cyclopentanediyl group and a cyclohexanediyl group; and a polycyclic cycloalkanediyl group including a norbornanediyl group and an adamantanediyl group. The cycloalkanediyl group is preferably a cycloalkanediyl group having a carbon number of 5 to 12.

Examples of the alkenediyl group include an ethenediyl group, a propenediyl group, and a butenediyl group. The alkenediyl group is preferably an alkenediyl group having a carbon number of 2 to 6.

Examples of the arenediyl group include phenylene, tolylene, and naphthylene groups. The arenediyl group is preferably an arenediyl group having a carbon atom number of 6 to 15.

Examples of the $R^{LA}$ group include the alkanediyl, cycloalkanediyl, alkenediyl, and arenediyl groups.

Among them, preferably, $R^8$ is an alkyl group having a carbon number of 1 to 4, and $R^9$ and $R^{10}$ are a monocyclic or polycyclic cycloalkane structure in which the alicyclic structure is obtained by combining $R^9$ and $R^{10}$ with the carbon atom to which they are bound. Preferably, $L^1$ is a single bond or —$R^{LA}$O—. Preferred $R^{LA}$ is an alkanediyl group.

Examples of the structural unit (I-1) include structural units represented by the following formulae (3-1) to (3-6) (hereinafter, also referred as "structural unit (I-1-1) to (I-1-6)").

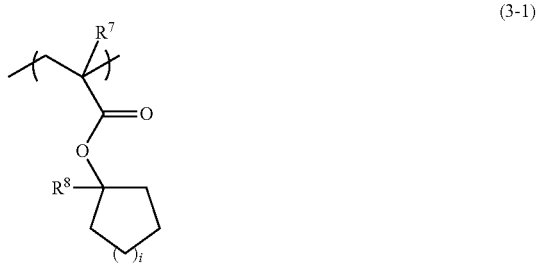

(3-1)

-continued (3-2)
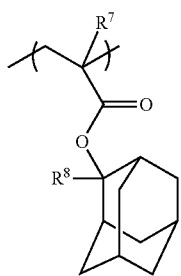

(3-3)
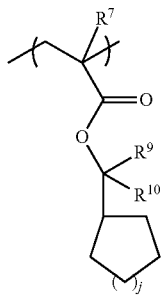

(3-4)
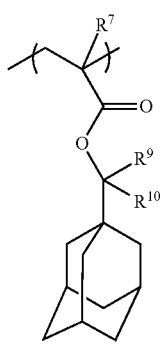

(3-5)
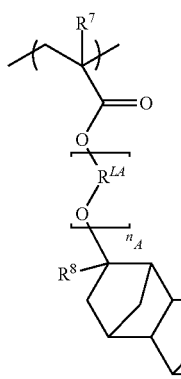

(3-6)
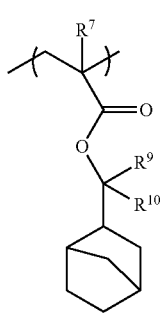

In the above formulae (3-1) to (3-6), $R^7$ to $R^{10}$ and $R^{LA}$ have the same meaning as in the above formula (2); and i and j are each independently an integer of 1 to 4. $n_A$ is 0 or 1.

i and j are preferably 1. $R^8$ to $R^{10}$ are preferably a methyl group, an ethyl group, or an iso-propyl group.

Examples of the structural unit represented by the formula (3-5) include structural units illustrated below, respectively.

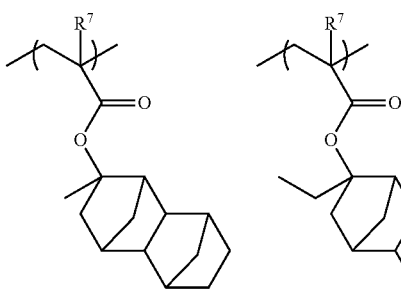

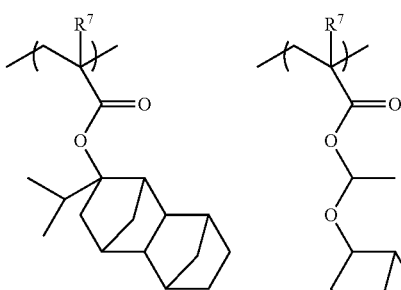

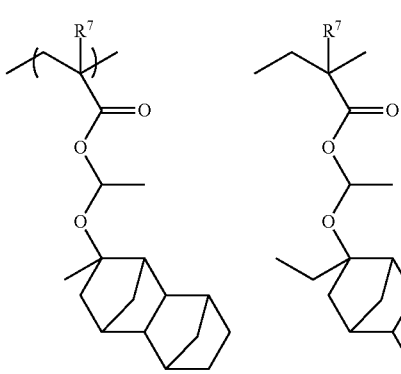

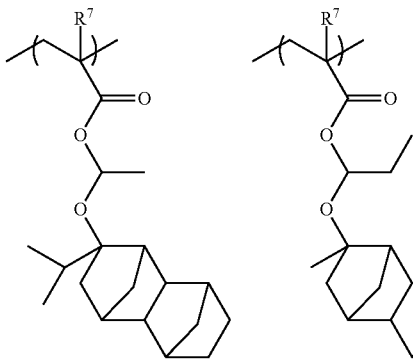

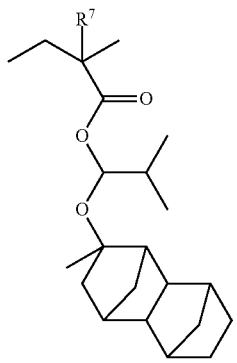

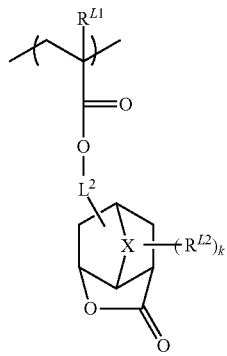 (T-1)

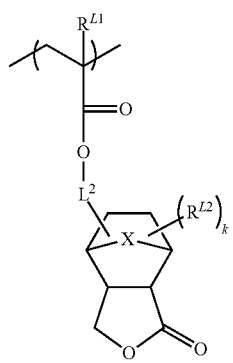 (T-2)

In each of the formulae, $R^7$ has the same meaning as in the formula (2).

Among them, the structural unit (I-1) is preferably the structural unit (I-1-1) or the structural unit (I-1-2), more preferably a structural unit having a cyclopentane structure or a structural unit having an adamantane structure, further preferably a structural unit derived from 1-alkylcyclopentyl (meth)acrylate, a structural unit derived from 2-alkyladamantyl (meth)acrylate, and particularly preferably a structural unit derived from 1-methylcyclohexyl (meth)acrylate or a structural unit derived from 2-ethyladamantyl (meth)acrylate.

The base resin may include one type of the structural unit (I), or two or more types of the structural units (I) in combination.

The lower limit of the content by percent of the structural unit (I) is preferably 5 mol %, more preferably 10 mol %, further preferably 20 mol %, and more further preferably 30 mol % based on the total structural units as the component of the base resin. The upper limit of the content by percent is preferably 95 mol %, more preferably 90 mol %, further preferably 80 mol %, and particularly preferably 70 mol %. By adjusting the content by percent of the structural unit (I) within the ranges, the patternability of the radiation-sensitive resin composition can be further improved.

[Structural Unit (II)]

The structural unit (II) is a structural unit including at least one selected from the group consisting of a lactone structure, a cyclic carbonate structure and a sultone structure. The solubility of the base resin into a developer can be adjusted by further introducing the structural unit (II). As a result, the radiation-sensitive resin composition can provide improved lithography properties such as the resolution. The adhesion between a resist pattern formed from the base resin and a substrate can also be improved.

Examples of the structural unit (II) include structural units represented by the following formulae (T-1) to (T-10).

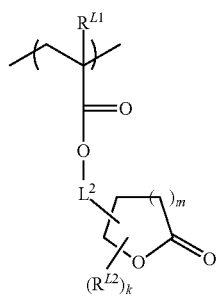 (T-3)

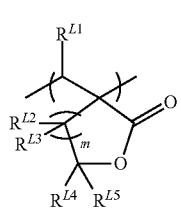 (T-4)

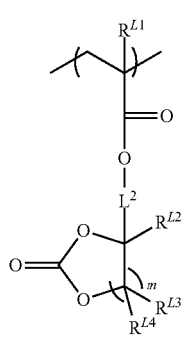 (T-5)

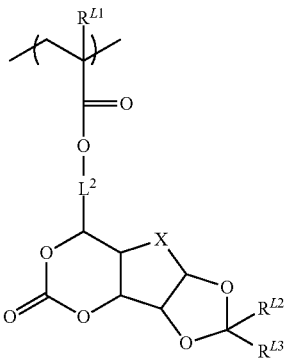 (T-6)

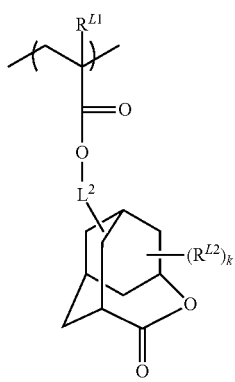 (T-7)

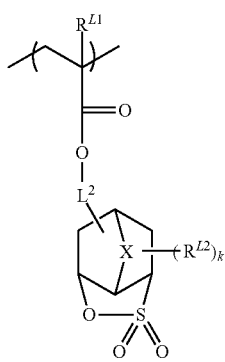 (T-8)

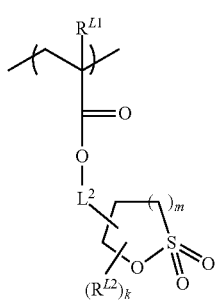 (T-9)

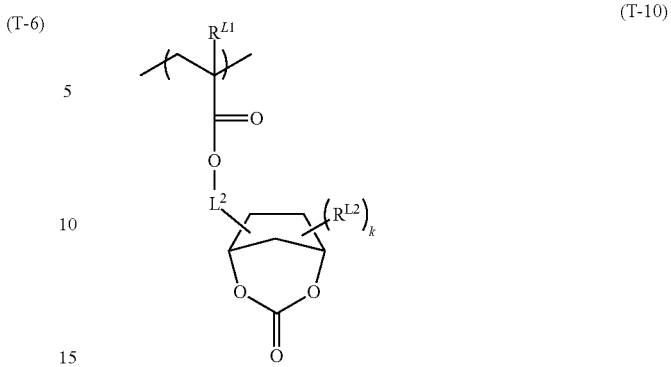 (T-10)

In the above formulae, $R^{L1}$ is a hydrogen atom, a fluorine atom, a methyl group, or a trifluoromethyl group; $R^{L2}$ to $R^{L5}$ are each independently a hydrogen atom, an alkyl group having a carbon number of 1 to 4, a cyano group, a trifluoromethyl group, a methoxy group, a methoxycarbonyl group, a hydroxy group, a hydroxymethyl group, or a dimethylamino group; $R^{L4}$ and $R^{L5}$ may be a divalent alicyclic group having a carbon number of 3 to 8, which is obtained by combining $R^{L4}$ and $R^{L5}$ with the carbon atom to which they are bound. $L^2$ is a single bond, or a divalent linking group; X is an oxygen atom or a methylene group; k is an integer of 0 to 3; and m is an integer of 1 to 3.

Example of the divalent alicyclic group having a carbon number of 3 to 8, which is composed of a combination of $R^{L4}$ and $R^{L5}$ with the carbon atom to which they are bound, includes the divalent alicyclic group having a carbon number of 3 to 8 in the divalent alicyclic group having a carbon number of 3 to 20, which is composed of a combination of the chain hydrocarbon group or the alicyclic hydrocarbon group represented by $R^9$ and $R^{10}$ in the above formula (2) with the carbon atom to which they are bound. One or more hydrogen atoms on the alicyclic group may be substituted with a hydroxy group.

Examples of the divalent linking group represented by $L^2$ as described above include a divalent straight or branched chain hydrocarbon group having a carbon number of 1 to 10; a divalent alicyclic hydrocarbon group having a carbon number of 4 to 12; and a group composed of one or more of the hydrocarbon group thereof and at least one group of —CO—, —O—, —NH— and —S—.

Among them, the structural unit (II) is preferably a group having a lactone structure, more preferably a group having a norbornane lactone structure, and further preferably a group derived from a norbornane lactone-yl (meth)acrylate.

The lower limit of the content by percent of the structural unit (II) is preferably 20 mol %, more preferably 25 mol %, and further preferably 30 mol % based on the total structural units as the component of the base resin. The upper limit of the content by percent is preferably 80 mol %, more preferably 70 mol %, and further preferably 60 mol %. By adjusting the content by percent of the structural unit (II) within the ranges, the radiation-sensitive resin composition can provide improved lithography properties such as the resolution. The adhesion between the formed resist pattern and the substrate can also be improved.

[Other Structural Units]

The base resin may also include any other structural unit in addition to the structural units (I) and (II). Example of the other structural unit includes a structural unit having a polar group, provided that the structural unit within the scope of the structural unit (II) is excluded. The base resin can adjust its solubility into the developer by further including the structural unit having a polar group in the resin. As a result, the radiation-sensitive resin composition can provide improved lithography properties such as the resolution. Examples of the polar group include a hydroxy group, a carboxy group, a cyano group, a nitro group, and a sulfonamide group. Among them, a hydroxy group or a carboxy group is preferred, and a hydroxy group is more preferred.

Example of the structural unit having a polar group includes structural units represented by the following formulae.

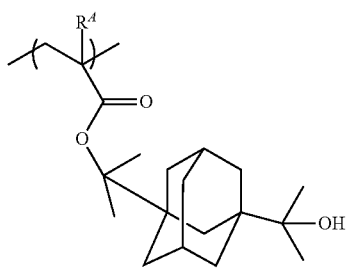
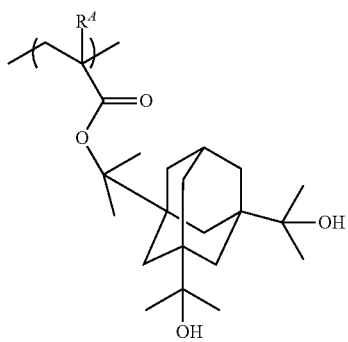
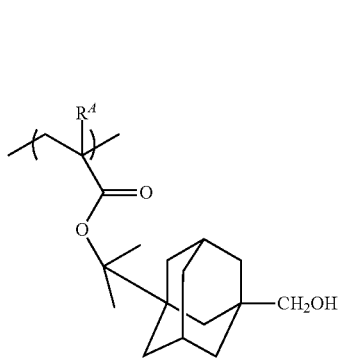
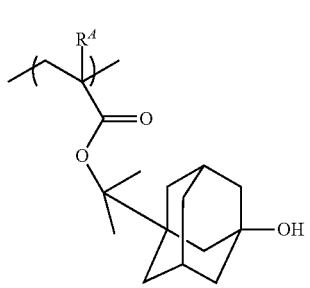

-continued

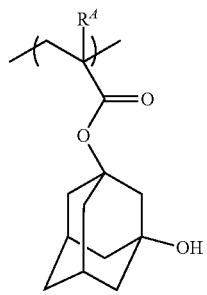
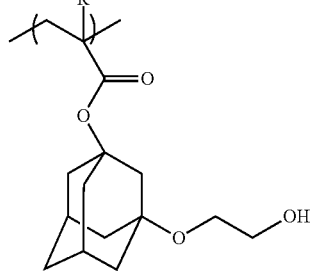
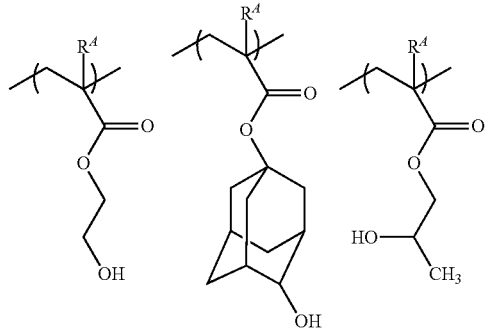
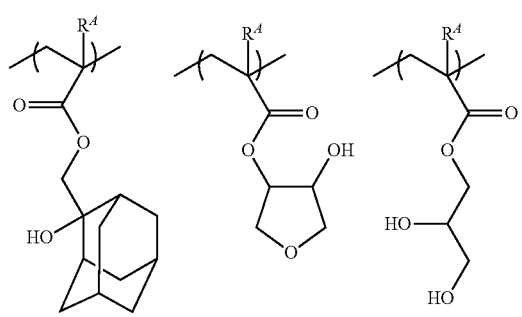
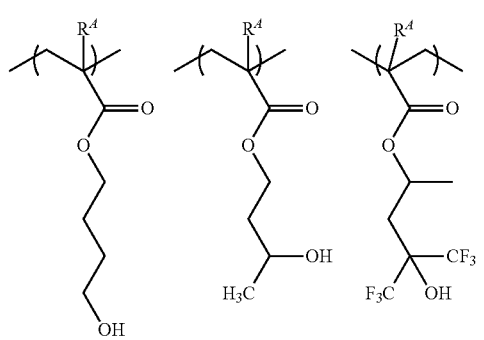

structural unit having a polar group. The structural unit (III) has low absorption in the very short wavelength range and high solubility of the resin in the exposed area. In particular, the resin can be suitably applied for a pattern formation by exposing to radiation having a wavelength of 50 nm or less, for example, an electron beam or EUV. In this case, the resin has preferably the structural unit (I) and the structural unit (III).

However, the polymerization of the hydroxystyrene is inhibited by the effect of its phenolic hydroxide group. Therefore, hydroxystyrene is polymerized in a state that the phenolic hydroxide group is preferably protected with a protecting group such as an acid-dissociable group, and then hydrolyzed for the deprotection of the phenolic hydroxide group to obtain the structural unit (III). The structural unit from which the structural unit (III) is obtained by the hydrolysis is preferably represented by the following formula (4).

In the above formula (4), $R^{11}$ is a hydrogen atom, a fluorine atom, a methyl group, or a trifluoromethyl group; $R^{12}$ is a monovalent hydrocarbon group having a carbon number of 1 to 20, or an alkoxy group. Example of the monovalent hydrocarbon group having a carbon number of 1 to 20 of $R^{12}$ includes the monovalent hydrocarbon group having a carbon number of 1 to 20 of $R^8$ in the structural unit (I). Examples of the alkoxy group include a methoxy group, an ethoxy group and a tert-butoxy group.

Preferred $R^{12}$ is an alkyl group and an alkoxy group. A methyl group or a tert-butoxy group is more preferred.

When the resin is for exposing to radiation having a wavelength of 50 nm or less, the lower limit of the content by percent of the structural unit (III) is preferably 20 mol %, and more preferably 30 mol % based on the total structural units as the component of the resin. The upper limit of the content by percent is preferably 80 mol %, and more preferably 70 mol %.

Synthesis Method of Base Resin

For example, the base resin can be synthesized by polymerizing each monomer for providing each structural unit with a radical polymerization initiator or the like in a suitable solvent.

Examples of the radical polymerization initiator include an azo-based radical initiator, including azobisisobutyronitrile (AIBN), 2,2'-azobis(4-methoxy-2,4-dimethylvaleronitrile), 2,2'-azobis(2-cyclopropylpropanenitrile), 2,2'-azobis (2,4-dimethylvaleronitrile), and dimethyl 2,2'-azobisisobutyrate; and peroxide-based radical initiator, including benzoyl peroxide, t-butyl hydroperoxide, and cumene hydroperoxide. Among them, AIBN or dimethyl In the above formulae, $R^A$ is a hydrogen atom, a fluorine atom, a methyl group, or a trifluoromethyl group.

When the base resin includes the structural unit having a polar group, the lower limit of the content by percent of the structural unit having a polar group is preferably 5 mol %, more preferably 10 mol %, and further preferably 20 mol % based on the total structural units as the component of the base resin. The upper limit of the content by percent is preferably 90 mol %, more preferably 80 mol %, and further preferably 70 mol %. By adjusting the content by percent of the structural unit having a polar group within the ranges, the radiation-sensitive resin composition can provide improved lithography properties such as the resolution.

The base resin may also include a structural unit derived from a hydroxystyrene (hereinafter, also referred as a "structural unit (III)") as the other structural unit in addition to the 2,2'-azobisisobutyrate is preferred, and AIBN is more preferred. The radical initiator may be used alone, or two or more radical initiators may be used in combination.

Examples of the solvent used for the polymerization include alkanes including n-pentane, n-hexane, n-heptane, n-octane, n-nonane, and n-decane;

cycloalkanes including cyclohexane, cycloheptane, cyclooctane, decalin, and norbornane;

aromatic hydrocarbons including benzene, toluene, xylene, ethylbenzene, and cumene;

halogenated hydrocarbons including chlorobutanes, bromohexanes, dichloroethanes, hexamethylenedibromide, and chlorobenzenes;

saturated carboxylate esters, including ethyl acetate, n-butyl acetate, i-butyl acetate, and methyl propionate;

ketones including acetone, methyl ethylketone, 4-methyl-2-pentanone, and 2-heptanone;

ethers including tetrahydrofuran, dimethoxyethanes, and diethoxyethanes; and alcohols including methanol, ethanol, 1-propanol, 2-propanol, and 4-methyl-2-pentanol. The solvent used for the polymerization may be used alone, or two or more solvents may be used in combination.

The reaction temperature of the polymerization is typically from 40° C. to 150° C., and preferably from 50° C. to 120° C. The reaction time is typically from 1 hour to 48 hours, and preferably from 1 hour to 24 hours.

Although the molecular weight of the base resin is not particularly limited, the weight average molecular weight (Mw) is preferably not less than 1,000 and not more than 50,000, more preferably not less than 2,000 and not more than 30,000, further preferably not less than 3,000 and not more than 15,000, and particularly preferably not less than 4,000 and not more than 12,000, as determined by Gel Permeation Chromatography (GPC) relative to standard polystyrene. If the Mw of the base resin is below the lower limits, the thermal resistance of the resulting resist film may be decreased. If the Mw of the base resin is beyond the upper limits, the developability of the resist film may be decreased.

For the base resin, the ratio of Mw to the number average molecular weight (Mn) as determined by GPC relative to standard polystyrene (Mw/Mn) is typically not less than 1 and not more than 5, preferably not less than 1 and not more than 3, and more preferably not less than 1 and not more than 2.

The Mw and Mn of the resin in the specification are amounts measured by using Gel Permeation Chromatography (GPC) with the condition as described below.

GPC column: two G2000HXL, one G3000HXL, and one G4000HXL (all manufactured from Tosoh Corporation)

Column temperature: 40° C.

Eluting solvent: tetrahydrofuran (manufactured from Wako Pure Chemical Corporation)

Flow rate: 1.0 mL/min

Sample concentration: 1.0% by mass

Sample injection amount: 100 μL

Detector: Differential Refractometer

Reference material: monodisperse polystyrene

The content of the base resin is preferably not less than 70% by mass, more preferably not less than 80% by mass, and further preferably not less than 85% by mass based on the total solid content of the radiation-sensitive resin composition.

(Other Resin)

The radiation-sensitive resin composition of this embodiment may include a resin having higher content by mass of fluorine atoms than the base resin as described above (hereinafter, also referred as a "high fluorine-containing resin") as the other resin. When the radiation-sensitive resin composition includes the high fluorine-containing resin, the high fluorine-containing resin can be localized on the surface layer of the resist film compared to the base resin. Therefore, the water repellency of the surface of the resist film can be improved during the immersion exposure.

The high fluorine-containing resin is preferably one having a structural unit represented by the following formula (5) (hereinafter, also referred to as a "structural unit (IV)") in addition to the structural unit (I) in the base resin as described above.

(5)

In the above formula (5), $R^{13}$ is a hydrogen atom, a methyl group, or a trifluoromethyl group; G is a single bond, an oxygen atom, a sulfur atom, —COO—, —SO$_2$ONH—, —CONH—, or —OCONH—; $R^{14}$ is a monovalent fluorinated chain hydrocarbon group having a carbon number of 1 to 20, or a monovalent fluorinated alicyclic hydrocarbon group having a carbon number of 3 to 20.

As $R^{13}$ as described above, in terms of the copolymerizability of monomers resulting in the structural unit (IV), a hydrogen atom or a methyl group is preferred, and a methyl group is more preferred.

As G as described above, in terms of the copolymerizability of monomers resulting in the structural unit (IV), a single bond or —COO— is preferred, and —COO— is more preferred.

Example of the monovalent fluorinated chain hydrocarbon group having a carbon number of 1 to 20 represented by $R^{14}$ as described above includes a group in which a part of or all of hydrogen atoms in the straight or branched chain alkyl group having a carbon number of 1 to 20 is/are substituted with a fluorine atom.

Example of the monovalent fluorinated alicyclic hydrocarbon group having a carbon number of 3 to 20 represented by $R^{14}$ as described above includes a group in which a part of or all of hydrogen atoms in the monocyclic or polycyclic hydrocarbon group having a carbon number of 3 to 20 is/are substituted with a fluorine atom.

The $R^{14}$ as described above is preferably a fluorinated chain hydrocarbon group, more preferably a fluorinated alkyl group, and further preferably 2,2,2-trifluoroethyl group, 1,1,1,3,3,3-hexafluoropropyl group and 5,5,5-trifluoro-1,1-diethylpentyl group.

When the high fluorine-containing resin has the structural unit (IV), the lower limit of the content by percent of the structural unit (IV) is preferably 10 mol %, more preferably 15 mol %, further preferably 20 mol %, and particularly preferably 25 mol % based on the total structural units as the component of the high fluorine-containing resin. The upper limit of the content by percent is preferably 60 mol %, more preferably 50 mol %, and further preferably 40 mol %. By adjusting the content by percent of the structural unit (IV) within the ranges, the content by mass percent of fluorine atoms of the high fluorine-containing resin can be suitably adjusted to promote the localization of the high fluorine-containing resin on the surface layer of the resist film. Therefore, the water repellency of the surface of the resist film can be improved during the immersion exposure.

The high fluorine-containing resin may include a structural unit having a fluorine atom represented by the following formula (f-2) (hereinafter, also referred as a "structural unit (V)") in addition to the structural unit (IV). The solubility of the high fluorine-containing resin into an alkaline developing solution can be improved by including the structural unit (f-2), and thereby prevent from generating the development defect.

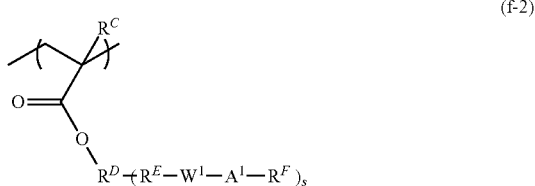

(f-2)

The structural unit (V) is classified into two groups: a unit having an alkali soluble group (x); and a unit having a group (y) in which the solubility into the alkaline developing solution is increased by the dissociation by alkali (hereinafter, simply referred as an "alkali-dissociable group"). In both cases of (x) and (y), $R^C$ in the above formula (f-2) is a hydrogen atom, a fluorine atom, a methyl group, or a trifluoromethyl group; $R^D$ is a single bond, a hydrocarbon group having a carbon number of 1 to 20 with the valency of (s+1), a structure in which an oxygen atom, a sulfur atom, —$NR^{dd}$—, a carbonyl group, —COO— or —CONH— is connected to the terminal on $R^E$ side of the hydrocarbon group, or a structure in which a part of hydrogen atoms in the hydrocarbon group is substituted with an organic group having a hetero atom; $R^{dd}$ is a hydrogen atom, or a monovalent hydrocarbon group having a carbon number of 1 to 10; and s is an integer of 1 to 3. However, when s is 1, there is no case that $R^D$ is a single bond.

When the structural unit (V) has the alkali soluble group (x), $R^F$ is a hydrogen atom; $A^1$ is an oxygen atom, —COO—* or —$SO_2O$—*; * refers to a bond to $R^F$; $W^1$ is a single bond, a hydrocarbon group having a carbon number of 1 to 20, or a divalent fluorinated hydrocarbon group. When $A^1$ is an oxygen atom, $W^1$ is a fluorinated hydrocarbon group having a fluorine atom or a fluoroalkyl group on the carbon atom connecting to $A^1$. $R^E$ is a single bond, or a divalent organic group having a carbon number of 1 to 20. When s is 2 or 3, a plurality of $R^E$, $W^1$, $A^1$ and $R^F$ may be each identical or different. The affinity of the high fluorine-containing resin into the alkaline developing solution can be improved by including the structural unit (V) having the alkali soluble group (x), and thereby prevent from generating the development defect. As the structural unit (V) having the alkali soluble group (x), particularly preferred is a structural unit in which $A^1$ is an oxygen atom and $W^1$ is a 1,1,1,3,3,3-hexafluoro-2,2-methanediyl group.

When the structural unit (V) has the alkali-dissociable group (y), $R^F$ is a monovalent organic group having carbon number of 1 to 30; $A^1$ is an oxygen atom, —$NR^{aa}$—, —COO—*, or —$SO_2O$—*; $R^{aa}$ is a hydrogen atom, or a monovalent hydrocarbon group having a carbon number of 1 to 10; * refers to a bond to $R^F$; $W^1$ is a single bond, or a divalent fluorinated hydrocarbon group having a carbon number of 1 to 20; $R^E$ is a single bond, or a divalent organic group having a carbon number of 1 to 20. When $A^1$ is —COO—* or —$SO_2O$—*, $W^1$ or $R^F$ has a fluorine atom on the carbon atom connecting to $A^1$ or on the carbon atom adjacent to the carbon atom. When $A^1$ is an oxygen atom, $W^1$ and $R^E$ are a single bond; $R^D$ is a structure in which a carbonyl group is connected at the terminal on $R^E$ side of the hydrocarbon group having a carbon number of 1 to 20; and $R^F$ is an organic group having a fluorine atom. When s is 2 or 3, a plurality of $R^E$, $W^1$, $A^1$ and $R^F$ may be each identical or different. The surface of the resist film is changed from hydrophobic to hydrophilic in the alkaline developing step by including the structural unit (V) having the alkali-dissociable group (y). As a result, the affinity of the high fluorine-containing resin into the alkaline developing solution can be significantly improved, and thereby prevent from generating the development defect more efficiently. As the structural unit (V) having the alkali-dissociable group (y), particularly preferred is a structural unit in which $A^1$ is —COO—*, and $R^F$ or $W^1$, or both is/are a fluorine atom.

In terms of the copolymerizability of monomers resulting in the structural unit (V), $R^C$ is preferably a hydrogen atom or a methyl group, and more preferably a methyl group.

When $R^E$ is a divalent organic group, $R^E$ is preferably a group having a lactone structure, more preferably a group having a polycyclic lactone structure, and further preferably a group having a norbornane lactone structure.

When the high fluorine-containing resin has the structural unit (V), the lower limit of the content by percent of the structural unit (V) is preferably 10 mol %, more preferably 20 mol %, further preferably 30 mol %, and particularly preferably 35 mol % based on the total structural units as the component of the high fluorine-containing resin. The upper limit of the content by percent is preferably 90 mol %, more preferably 75 mol %, and further preferably 60 mol %. By adjusting the content by percent of the structural unit (V) within the ranges, the water repellency of the surface of the resist film can be further improved during the immersion exposure.

The lower limit of Mw of the high fluorine-containing resin is preferably 1,000, more preferably 2,000, further preferably 3,000, and particularly preferably 5,000. The upper limit of Mw is preferably 50,000, more preferably 30,000, further preferably 20,000, and particularly preferably 15,000.

The lower limit of the Mw/Mn of the high fluorine-containing resin is typically 1, and more preferably 1.1. The upper limit of the Mw/Mn is typically 5, preferably 3, more preferably 2, and further preferably 1.7.

The lower limit of the content of the high fluorine-containing resin is preferably 0.1% by mass, more preferably 0.5% by mass, further preferably 1% by mass, and even further preferably 1.5% by mass based on the total solid content of the radiation-sensitive resin composition. The upper limit of the content is preferably 20% by mass, more preferably 15% by mass, further preferably 10% by mass, and particularly preferably 7% by mass.

The lower limit of the content of the high fluorine-containing resin is preferably 0.1 part by mass, more preferably 0.5 part by mass, further preferably 1 part by mass, and particularly preferably 1.5 part by mass based on 100 parts by mass of total base resins. The upper limit of the content is preferably 15 parts by mass, more preferably 10 parts by mass, further preferably 8 parts by mass, and particularly preferably 5 parts by mass.

By adjusting the content of the high fluorine-containing resin within the ranges, the high fluorine-containing resin can be localized on the surface layer of the resist film more efficiently. Therefore, the water repellency of the surface of the resist film can be improved during the immersion exposure. The radiation-sensitive resin composition may contain one type of the high fluorine-containing resin, or two or more high fluorine-containing resins in combination.

(Method for Synthesizing High Fluorine-Containing Resin)

The high fluorine-containing resin can be synthesized by the similar method for the base resin as described above.

(Onium Salt Compound)

The onium salt compound is represented by the following formula (1):

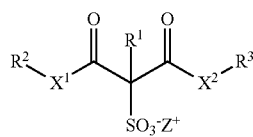

(1)

In the formula (1), $Z^+$ is a monovalent onium cation;

$R^1$ is a hydrogen atom or a monovalent group provided that the monovalent group represented by $R^1$ is not a fluoro group or a monovalent organic group containing a fluorine atom;

$X^1$ and $X^2$ are each independently a single bond, —O—, —S— or —NR'— wherein R' is a hydrogen atom or a monovalent hydrocarbon group, provided that when two R's are present, the two R's are the same or different; and in a case where $X^1$ is —NR'—, $R^2$ is a monovalent organic group or a hydrogen atom, in a case where $X^2$ is —NR'—, $R^3$ is a monovalent organic group or a hydrogen atom, in a case where neither $X^1$ nor $X^2$ is —NR'—, $R^2$ and $R^3$ are each independently a monovalent organic group, optionally, in a case where $X^1$ is —NR'—, $R^2$ is linked to R' in $X^1$ to form a cyclic structure, optionally, in a case where $X^2$ is —NR'—, $R^3$ is linked to R' in $X^2$ to form a cyclic structure, and $R^2$ and $R^3$ are optionally linked with each other to form a cyclic structure.

In the onium salt compound, neither a fluorine atom nor a group containing a fluorine atom (hereinafter the two will be collectively referred to also as a "fluorine-atom-containing group") is introduced to each of the α-position carbon atom and the β-position carbon atom of $SO_3^-$. In this way, a lowering in the fluorination degree can be promoted. By the stabilization effect of sulfonate ions of the carbonyl groups bonded, respectively, to both sides of the α-position carbon atom, an acid having a sufficient acid strength can be generated, even in the case of not introducing any fluorine-atom-containing group into the salt compound, this group being unavoidably introduced into such a compound in the prior art to improve the acid strength.

The monovalent group represented by $R^1$ is not particularly limited as far as the group contains no fluorine-atom-containing group. The monovalent group is, for example, a monovalent electron-withdrawing group which contains no fluorine atom, or a monovalent organic group which is different from this electron-withdrawing group and contains no fluorine atom. In the monovalent organic group, any hydrogen atom thereof, or any carbon atom in a skeleton thereof may be substituted with a heteroatom (examples thereof not including a fluorine atom).

Examples of the monovalent electron-withdrawing group containing no fluorine atom include:

acyl groups such as acetyl, propionyl, benzoyl, and acryloyl groups;

alkylsulfonyl groups such as a methylsulfonyl group;

a cyano group;

a nitro group;

halogen radicals such as chlorine, bromine, and iodine atoms (examples thereof not including a fluorine atom); and any monovalent hydrocarbon group having a carbon atom number of 1 to 5 in which hydrogen atoms are partially or wholly substituted with at least one species of the atoms and groups.

Examples of the monovalent hydrocarbon group having a carbon atom number of 1 to 5 include:

monovalent chain hydrocarbon groups such as alkyl groups, for example, methyl, ethyl, propyl and butyl groups, alkenyl groups, for example, ethenyl, propenyl and butenyl groups, and alkynyl groups, for example, ethynyl, propynyl and butynyl groups; and monovalent alicyclic hydrocarbon groups such as cycloalkyl groups, for example, cyclopropyl, cyclobutyl and cyclopentyl, and cycloalkenyl groups, for example, cyclopropenyl, cyclobutenyl and cyclopentenyl groups.

Examples of the monovalent organic group different from the monovalent electron-withdrawing group include:

alkoxy groups such as methoxyl, ethoxy, and tert-butoxy groups;

aryloxy groups such as phenoxy and p-tolyloxy groups;

alkylthiooxy groups such as methylthiooxy, ethylthiooxy, and tert-butylthiooxy groups;

arylthiooxy groups such as phenylthioxy, and p-tolylthioxy groups;

alkoxycarbonyl groups such as methoxycarbonyl, butoxycarbonyl, and adamantylmethyloxycarbonyl groups;

aryloxycarbonyl groups such as a phenoxycarbonyl group;

alkylcarbonyl groups or cycloalkylcarbonyl groups such as acetoxy, cyclohexylcarbonyl, and adamantylcarbonyl groups;

straight chain or branched chain alkyl groups such as methyl, ethyl, propyl, butyl, heptyl, hexyl, dodecyl, and 2-ethylhexyl groups;

alkenyl groups such as vinyl, propenyl, and hexenyl groups;

alkynyl groups such as ethynyl, propynyl, and hexynyl groups;

cycloalkyl groups such as cyclopentyl, and cyclohexyl groups;

polycyclic cycloalkyl groups such as norbornyl, adamantyl, tricyclodecyl, and tetracyclododecyl groups;

cycloalkenyl groups such as cyclopropenyl, cyclobutenyl, cyclopentenyl, and cyclohexenyl groups;

polycyclic cycloalkenyl groups such as norbornenyl, tricyclodecenyl, and tetracyclododecenyl groups;

aryl groups such as phenyl, o-tolyl, m-tolyl, p-tolyl, p-hydroxyphenyl, p-trifluoromethylphenyl, and 1-naphthyl, and 1-anthracenyl groups;

aralkyl groups such as benzyl, 1-phenylethyl, 2-phenylethyl, 1-phenylpropyl, 2-phenylpropyl, 3-phenylpropyl, l-naphthylmethyl, and 2-naphthylmethyl groups;

monocyclic or polycyclic lactone groups having a carbon atom number of 3 to 30 in which one hydrogen atom is eliminated from any one of the following: γ-butyrolactone, γ-valerolactone, angelicalactone, γ-hexalactone, γ-heptalactone, γ-octalactone, γ-nonalactone, 3-methyl-4-octanolyde (whisky lactone), γ-decalactone, γ-undecalactone, γ-dodecalactone, γ-jasmolactone (7-decenolactone), δ-hexalactone, 4,6,6 (4,4,6)-trimethyltetrahydropyran-2-one, δ-octalactone, δ-nanolactone, δ-decalactone, δ-2-decenolactone, δ-undecalactone, δ-dodecalactone, δ-tridecalactone, δ-tetradecalactone, lactoskatone, ε-decalactone, ε-dodecalactone, cyclohexyllactone, jasminelactone, cis-jasmonelactone, methyl γ-decalactone;

oxoalkyl groups having a carbon atom number of 2 to 20, and oxocycloalkyl groups having a carbon atom number of 6 to 10, such as 2-oxo-propyl, 2-oxo-butyl, 2-oxo-3-methyl-butyl, 2-oxo-pentyl, 2-oxo-3-methyl-pentyl, 2-oxo-4-methyl-pentyl, 2-oxo-3-ethyl-pentyl, 2-oxo-hexyl, 2-oxo-3-methyl-hexyl, 2-oxo-4-methyl-hexyl, 2-oxo-5-methyl-hexyl, 2-oxo-3-ethyl-hexyl, 2-oxo-4-ethyl-hexyl, 2-oxo-heptyl, 2-oxo-3-methyl-heptyl, 2-oxo-4-methyl-heptyl, 2-oxo-5-methyl-heptyl, 2-oxo-6-methyl-heptyl, 2-oxo-3-ethyl-heptyl, 2-oxo-4-ethyl-heptyl, 2-oxo-5-ethyl-heptyl, 2-oxo-3-propyl-heptyl, 2-oxo-4-propyl-heptyl, 2-oxo-octyl, 2-oxo-3-methyl-octyl, 2-oxo-4-methyl-octyl, 2-oxo-5-methyl-octyl, 2-oxo-6-methyl-octyl, 2-oxo-7-methyl-octyl, 2-oxo-3-ethyl-octyl, 2-oxo-4-ethyl-octyl, 2-oxo-5-ethyl-octyl, 2-oxo-cyclopentyl, 2-oxo-cyclohexyl, 2-oxo-cycloheptyl, 2-oxo-cyclopropylmethyl, 2-oxo-methylcyclohexyl, 2-oxo-cyclohexylmethyl, 2-oxo-norbornyl, and 2-oxo-bornyl;

a carbamoyl group;

a hydroxy group; and a carboxy group.

The monovalent group represented by $R^1$ is preferably a hydrogen atom or a monovalent electron-withdrawing group from the viewpoint of the easiness of the synthesis of the onium salt compound represented by the formula (1), and the acid strength of the acid to be generated.

When $X^1$ and $X^2$ are each —NR'—, the monovalent hydrocarbon group represented by R' may be preferably the same monovalent hydrocarbon group as represented by $R^8$ in the formula (2).

In a case where $X^1$ is —NR'—, $R^2$ and R' may be a hydrogen atom. In a case where $X^2$ is —NR'—, $R^3$ and R' may be a hydrogen atom. In other words, in this case, one or both of —$X^1$—$R^2$ and —$X^2$—$R^3$ may be —$NH_2$.

Optionally, in a case where $X^1$ is —NR'—, $R^2$ is linked to R' in $X^1$ to form a cyclic structure, and optionally, in a case where $X^2$ is —NR'—, $R^3$ is linked to R' in $X^2$ to form a cyclic structure. Examples of the cyclic structure include heterocyclic amines, such as pyrrolidine, pyrrole, piperidine, pyridine, and pyrimidine rings.

The monovalent organic group represented by each of $R^2$ and $R^3$ may be preferably the same monovalent organic group as represented by $R^1$ in the formula (1), or a group in which any carbon atom in a skeleton of this organic group is substituted with a hetero atom. The carbon in the skeleton may be carbonyl carbon. This organic group may have a substituent. The substituent may be, for example, a halogen atom (examples thereof including a fluorine atom); an alkyl group (which may be in the form of any one of straight chain, branched chain, and cyclic forms, and preferably has a carbon atom number of 1 to 12); an aryl group (preferably having a carbon atom number of 6 to 14); or a hydroxy, alkoxy, ester, amide, urethane, ureido, thioether, sulfonamide or sulfonic acid ester group.

At least one of $R^2$ and $R^3$ preferably has a cyclic structure. When the onium salt compound has a cyclic structure, the diffusion length of the generated acid can be adjusted into an appropriate range to improve various resist performances.

At least one of $R^2$ and $R^3$ may be an alicyclic hydrocarbon group having a carbon atom number of 3 to 20. The alicyclic hydrocarbon group may be monocyclic or polycyclic. Preferred are monocyclic cycloalkyl groups such as cyclopentyl, cyclohexyl, and cyclooctyl groups, and polycyclic cycloalkyl groups such as norbornyl, norbornene-yl, tricyclodecanyl (such as tricyclo[5.2.1.0 (2,6)]decanyl), tetracyclodecanyl, tetracyclododecanyl, and adamantyl groups. Any one of the carbon atoms constituting the organic group containing a cyclic structure (the carbon atoms contributing to the formation of the cycle) may be a carbonyl carbon atom.

At least one of $R^2$ and $R^3$ may be a group containing at least one structure selected from the group consisting of a lactone structure, a cyclic carbonate structure, a cyclic acetal, a cyclic ether and a sultone structure. Examples of the group include heterocycle structures represented by formulae illustrated below, respectively (in the formulae illustrated below, each * is a hand bonding to $X^1$ or $X^2$; the same applies hereinafter).

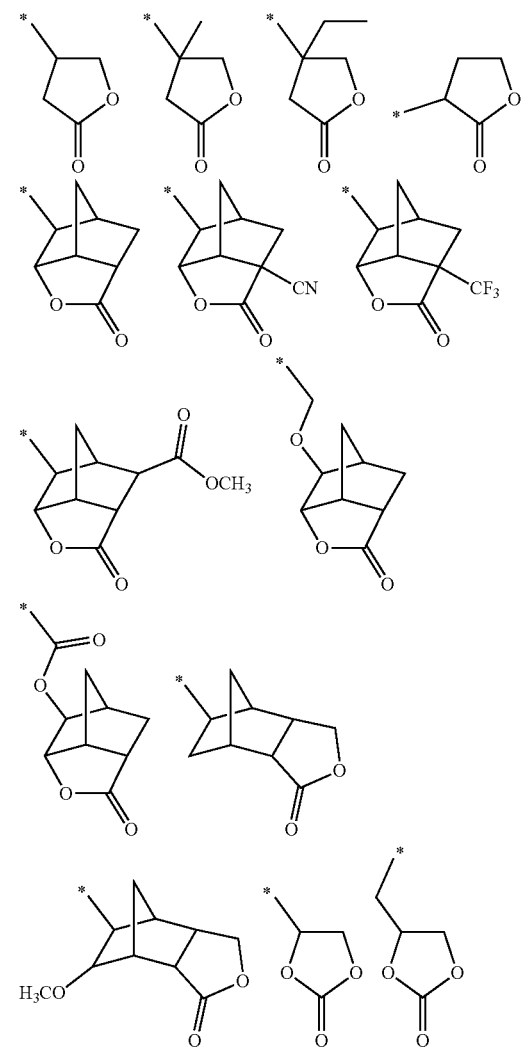

-continued

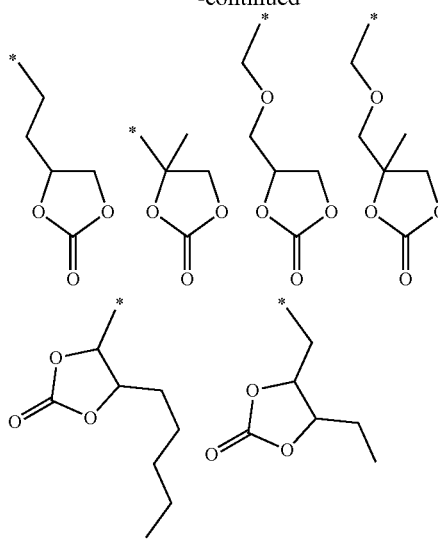
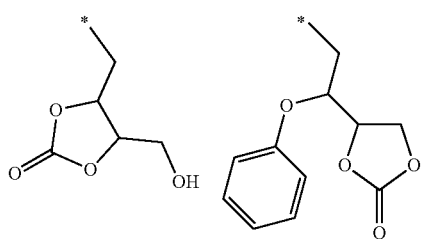
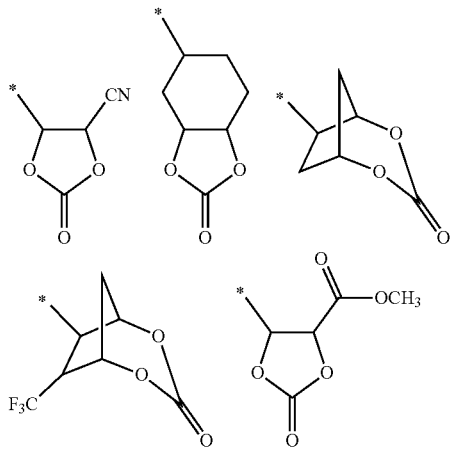
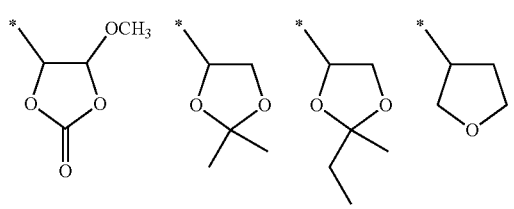
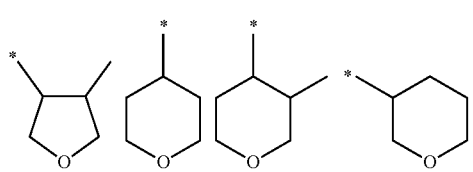

-continued

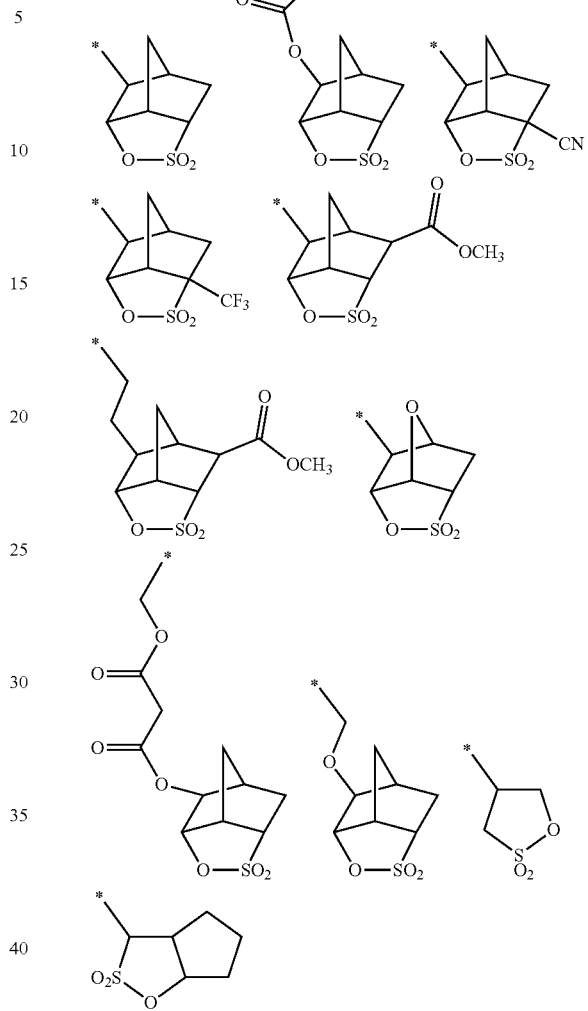

At least one of $R^2$ and $R^3$ may be an aromatic hydrocarbon group having a carbon atom number of 6 to 20. Examples of the monovalent aromatic hydrocarbon group having a carbon atom number of 6 to 20 include aryl groups such as phenyl, tolyl, xylyl, naphthyl, anthryl and fluorenyl groups; and aralkyl groups such as benzyl, phenethyl and naphthylmethyl groups.

It is allowable that neither $R^2$ nor $R^3$ has a cyclic structure, and at least one of $R^2$ and $R^3$ is a chain hydrocarbon group which has a carbon atom number of 1 to 20 and which is optionally substituted with at least one substituent selected from the group consisting of a halogen atom and a polar group. Even when neither $R^2$ nor $R^3$ has a cyclic structure, the diffusion length of the acid to be generated can be appropriately controlled to exhibit desired various resist performances by hydrogen bonding or van den Waals force between the halogen atom or polar group and the hydrogen atom of the resin.

Examples of the halogen atom include fluorine, bromine, chlorine, and iodine atoms. A fluorine atom is particularly preferred. Examples of the polar group include hydroxy, keto (=O), carboxy, nitro, cyano, sulfonamide, and 1,3- diketo groups. Among these groups, hydroxy, keto and carboxy groups are preferred, and a hydroxy group is more preferred.

Preferred examples of the chain hydrocarbon group which has a carbon atom number of 1 to 20 and which may be substituted with at least one of a halogen atom and a polar group are represented by formulae illustrated below.

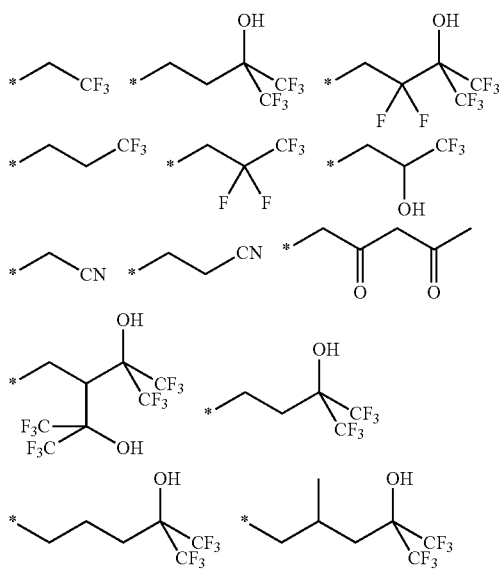

(Onium Cation)

The onium cation is a cation degradable by irradiating with a radioactive ray. In the exposed part, a sulfonic acid is generated by reacting a proton generated by degradation of the radiation degradable onium cation with the sulfonate anion (A) as described above. Examples of the radioactive ray include ultraviolet ray, far ultraviolet ray, extreme ultraviolet ray (EUV); an electromagnetic wave including X ray and γ ray; an electron beam; and a charged particle radiation such as a ray. Among them, far ultraviolet ray, EUV, or an electron beam is preferred. The far ultraviolet ray is preferably KrF excimer laser light (wavelength is 248 nm) or ArF excimer laser light (wavelength is 193 nm), and more preferably ArF excimer laser light.

Examples of the onium cation include a radiation degradable onium cation, including S, I, O, N, P, Cl, Br, F, As, Se, Sn, Sb, Te, and Bi. Among them, a sulfonium cation having S (sulfur) as an element or an iodonium cation having I (iodine) as an element is preferred, and cations represented by the following formulae (X-1) to (X-5) are more preferred.

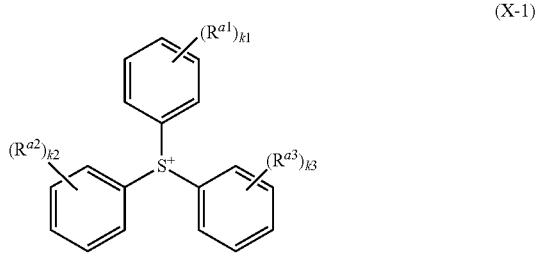

(X-1)

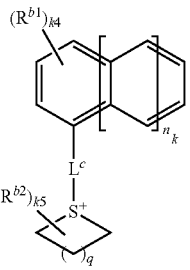

(X-2)

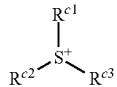

(X-3)

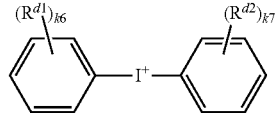

(X-4)

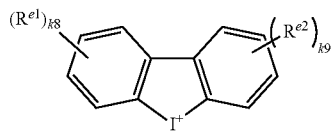

(X-5)

In the above formula (X-1), $R^{a1}$, $R^{a2}$ and $R^{a3}$ are each independently a substituted or unsubstituted, straight or branched chain alkyl group, alkoxy group or alkoxycarbonyloxy group having a carbon number of 1 to 12; a substituted or unsubstituted, monocyclic or polycyclic cycloalkyl group having a carbon number of 3 to 12; a substituted or unsubstituted aromatic hydrocarbon group having a carbon number of 6 to 12; a hydroxy group, —$OSO_2$—$R^P$, —$SO_2$—$R^Q$ or —S—$R^T$; or a ring structure obtained by combining two or more of these groups. $R^P$, $R^Q$ and $R^T$ are each independently a substituted or unsubstituted, straight or branched chain alkyl group having a carbon number of 1 to 12; a substituted or unsubstituted alicyclic hydrocarbon group having a carbon number of 5 to 25; and a substituted or unsubstituted aromatic hydrocarbon group having a carbon number of 6 to 12. k1, k2 and k3 are each independently an integer of 0 to 5. When there are a plurality of $R^{a1}$ to $R^{a3}$ and a plurality of $R^P$, $R^Q$ and $R^T$, a plurality of $R^{a1}$ to $R^{a3}$ and a plurality of $R^P$, $R^Q$ and $R^T$ may be each identical or different.

In the above formula (X-2), $R^{b1}$ is a substituted or unsubstituted, straight chain or branched alkyl group or alkoxy group having a carbon number of 1 to 20; a substituted or unsubstituted acyl group having a carbon number of 2 to 8; or a substituted or unsubstituted aromatic hydrocarbon group having a carbon number of 6 to 8; or a hydroxy group. $n_k$ is 0 or 1. When $n_k$ is 0, k4 is an integer of 0 to 4. When $n_k$ is 1, k4 is an integer of 0 to 7. When there are a plurality of $R^{b1}$, a plurality of $R^{b1}$ may be each identical or different. A plurality of $R^{b1}$ may represent a ring structure obtained by combining them. $R^{b2}$ is a substituted or unsubstituted, straight chain or branched alkyl group having a carbon number of 1 to 7; or a substituted or unsubstituted aromatic hydrocarbon group having a carbon number of 6 to 7. k5 is an integer of 0 to 4. When there are a plurality of $R^{b2}$, a plurality of $R^{b2}$ may be each identical or different. A plurality of $R^{b2}$ may represent a ring structure obtained by combining them. q is an integer of 0 to 3.

In the above formula (X-3), $R^{c1}$, $R^{c2}$ and $R^{c3}$ are each independently a substituted or unsubstituted, straight or branched chain alkyl group having a carbon number of 1 to 12; or a substituted or unsubstituted aromatic hydrocarbon group having a carbon number of 6 to 12.

In the above formula (X-4), $R^{d1}$ and $R^{d2}$ are each independently a substituted or unsubstituted, straight or branched chain alkyl group, alkoxy group or alkoxycarbonyl group having a carbon number of 1 to 12; a substituted or unsubstituted aromatic hydrocarbon group having a carbon number of 6 to 12; a halogen atom; a halogenated alkyl group having a carbon number of 1 to 4; a nitro group; or a ring structure obtained by combining two or more of these groups. k6 and k7 are each independently an integer of 0 to 5. When there are a plurality of $R^{d1}$ and a plurality of $R^{d2}$, a plurality of $R^{d1}$ and a plurality of $R^{d2}$ may be each identical or different.

In the above formula (X-5), $R^{e1}$ and $R^{e2}$ are each independently a halogen atom; a substituted or unsubstituted straight or branched chain alkyl group having a carbon number of 1 to 12; or a substituted or unsubstituted aromatic hydrocarbon group having a carbon number of 6 to 12. k8 and k9 are each independently an integer of 0 to 4.

In each of the formulae illustrated above, examples of each of the groups are as follows:

Examples of the unsubstituted straight chain alkyl group include methyl, ethyl, n-propyl, and n-butyl groups.

Examples of the unsubstituted branched chain alkyl group include i-propyl, i-butyl, sec-butyl, and t-butyl groups.

Examples of the unsubstituted straight chain alkoxy group include methoxy, ethoxy, n-propoxy, and n-butoxy groups.

Examples of the unsubstituted branched chain alkoxy group include i-propoxy, i-butoxy, sec-butoxy, and t-butoxy groups.

Examples of the unsubstituted straight chain alkoxycarbonyloxy group include methoxycarbonyloxy, ethoxycarbonyloxy, n-propoxycarbonyloxy, and n-butoxycarbonyloxy groups.

Examples of the unsubstituted branched chain alkoxycarbonyloxy group include i-propoxycarbonyloxy, i-butoxycarbonyloxy, sec-butoxycarbonyloxy, and t-butoxycarbonyloxy groups.

Examples of the unsubstituted monocyclic or polycyclic cycloalkyl group include monocyclic cycloalkyl groups such as cyclopropyl, cyclobutyl, cyclopentyl and cyclohexyl groups; and polycyclic cycloalkyl groups such as norbornyl, adamantyl, tricyclodecyl and tetracyclododecyl groups.

Examples of the unsubstituted aromatic hydrocarbon group include aryl groups such as phenyl, and naphthyl groups.

Examples of the unsubstituted acyl group include acetyl, propionyl, butanoyl, pentanoyl, and benzoyl groups.

Examples of the unsubstituted straight chain alkoxycarbonyl group include methoxycarbonyl, ethoxycarbonyl, n-propoxycarbonyl, and n-butoxycarbonyl groups.

Examples of the unsubstituted branched chain alkoxycarbonyl group include i-propoxycarbonyl, i-butoxycarbonyl, sec-butoxycarbonyl, and t-butoxycarbonyl groups.

Examples of the halogenated alkyl group include a trifluoromethyl group.

Examples of a substituent group with which an hydrogen atom in the group as described above may be substituted include a halogen atom, including a fluorine atom, a chlorine atom, a bromine atom, an iodine atom; a hydroxy group, a carboxy group, a cyano group, a nitro group, an alkyl group (when a hydrogen atom in a cycloalkyl group or an aromatic hydrocarbon group is substituted), an aryl group (when a hydrogen atom in an alkyl group is substituted), an alkoxy group, an alkoxycarbonyl group, an alkoxycarbonyloxy group, an acyl group, and an acyloxy group. Among them, a hydroxy group, an alkoxy group, an alkoxycarbonyl group, an alkoxycarbonyloxy group, an acyl group, or an acyloxy group is preferred. An alkoxy group or an alkoxycarbonyl group is more preferred.

Examples of the onium salt compound represented by the formula (1) include compounds represented by formulae (1-1) to (1-27), respectively (the compounds may be referred to as the "onium salt compounds (1-1) to (1-27)").

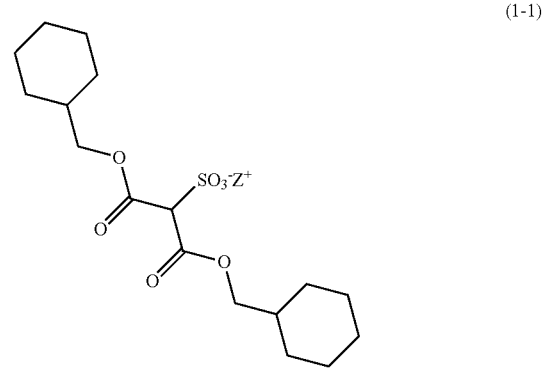

(1-1)

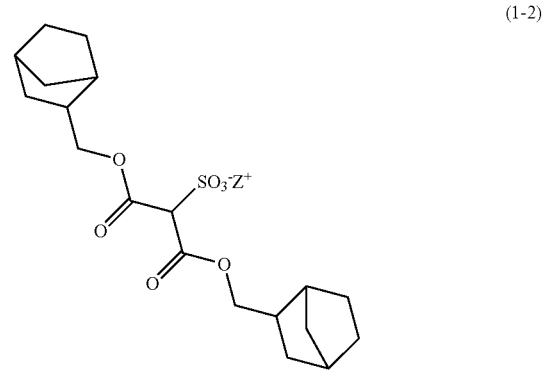

(1-2)

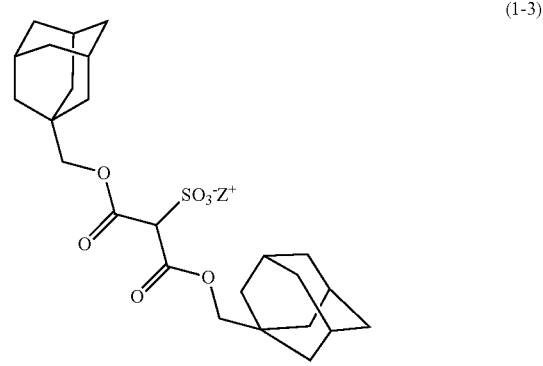

(1-3)

(1-4)
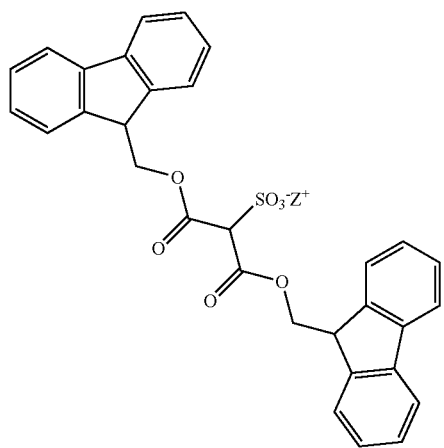
(1-5)
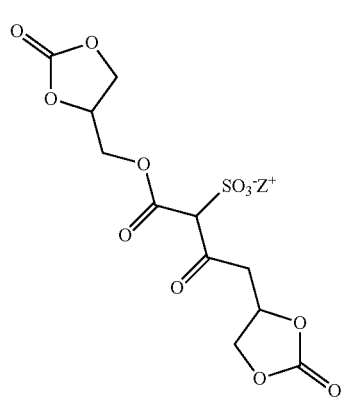
(1-6)
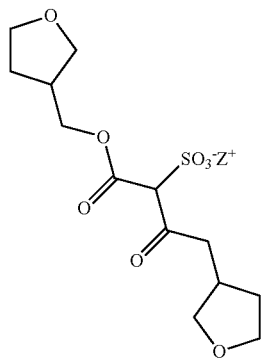
(1-7)
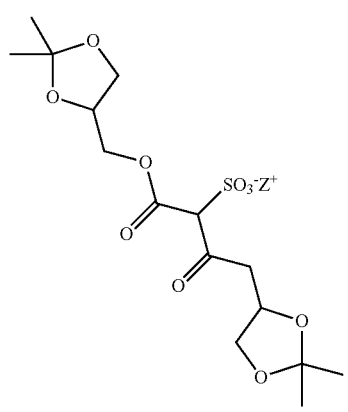
(1-8)
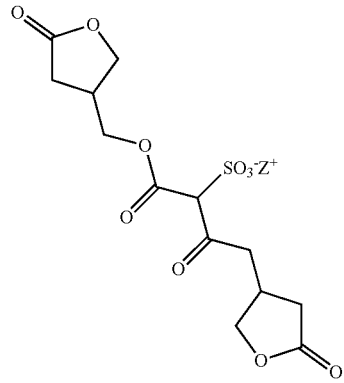
(1-9)
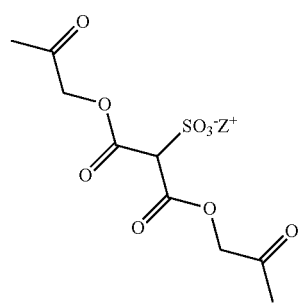
(1-10)
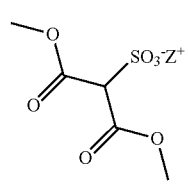
(1-11)
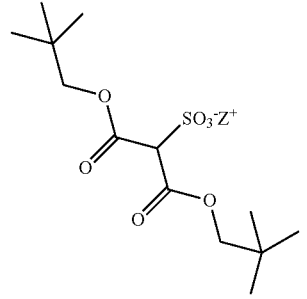
(1-12)
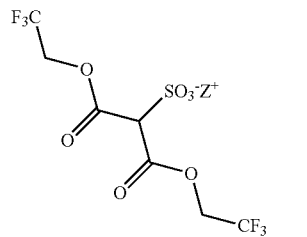

(1-13)
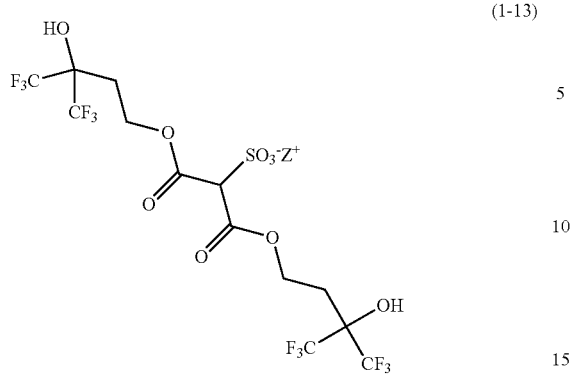
(1-17)
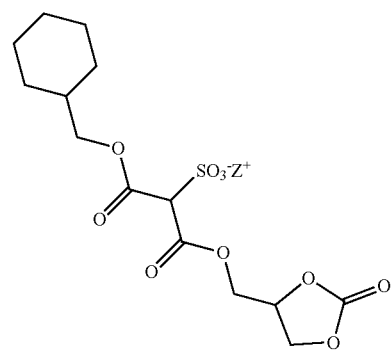
(1-14)
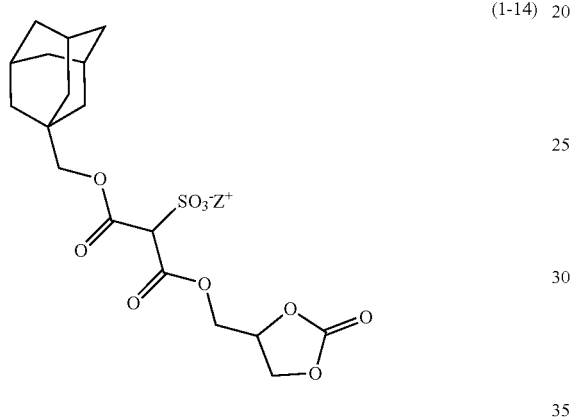
(1-18)
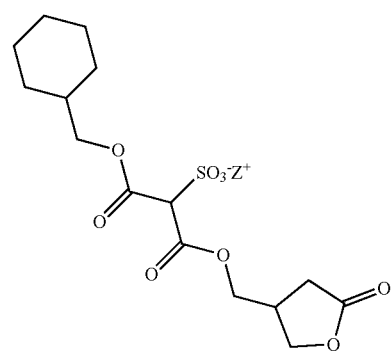
(1-15)
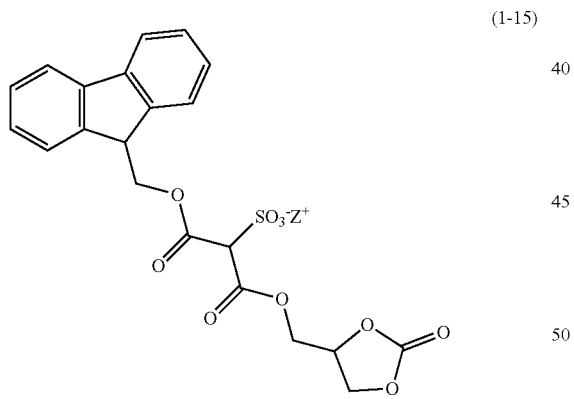
(1-19)
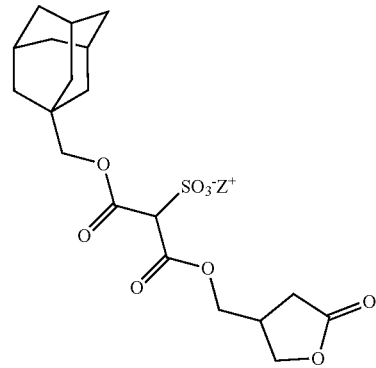
(1-16)
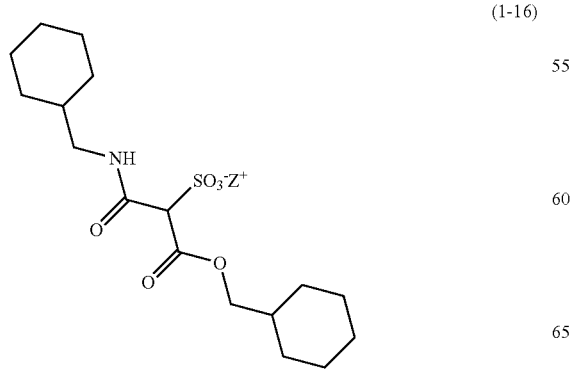
(1-20)
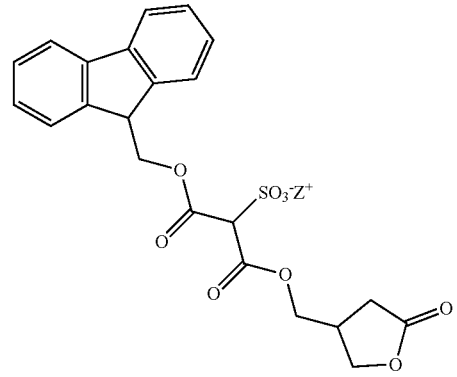

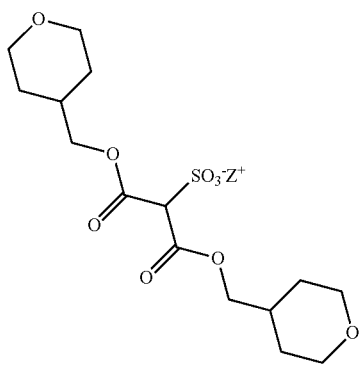 (1-21)

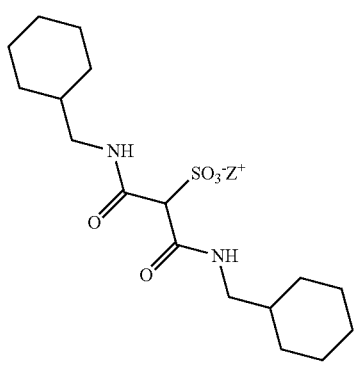 (1-22)

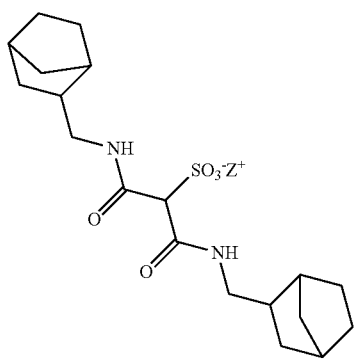 (1-23)

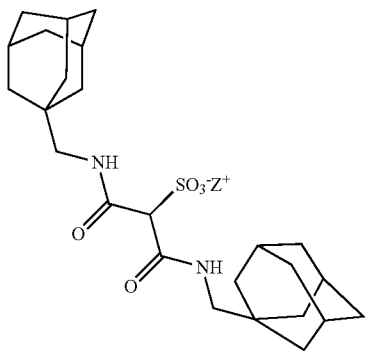 (1-24)

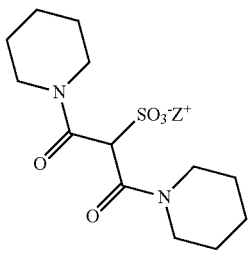 (1-25)

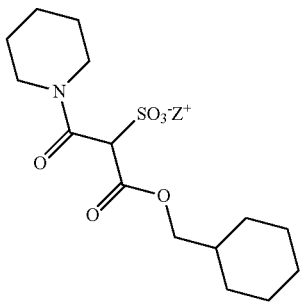 (1-26)

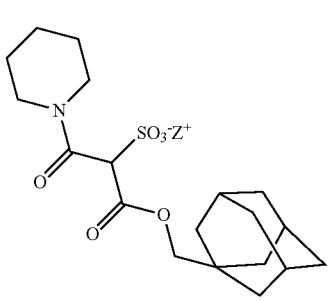 (1-27)

In each of the formulae (1-1) to (1-27), $Z^+$ is a monovalent onium cation.

Among these examples, the compounds (1-1) to (1-16) are preferred.

The lower limit of the content of the onium salt compound in the radiation-sensitive resin composition of the present embodiment is preferably 3 parts, more preferably 5 parts, even more preferably 7 parts, in particular preferably 9 parts by mass for 100 parts by mass of the baser resin. The upper limit of the content is preferably 30 parts, more preferably 27 parts, even more preferably 24 parts, in particular preferably 20 parts by mass therefor. When the content of the onium salt compound is set into any one of these ranges, a resist pattern can be formed which is excellent in various resist performances.

(Method for Synthesizing Onium Salt Compound)

In the present embodiment, the onium salt compound can be synthesized in accordance with a scheme described below when the compound is, for example, a compound in which $R^1$ in the formula (1) is a hydrogen atom, $X^1$ and $X^2$ are each O, and $Z^+$ is a sulfonium cation represented by the formula (i-1).

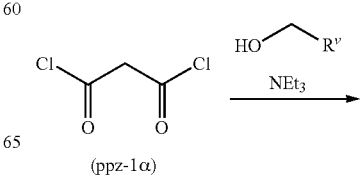

(ppz-1α)

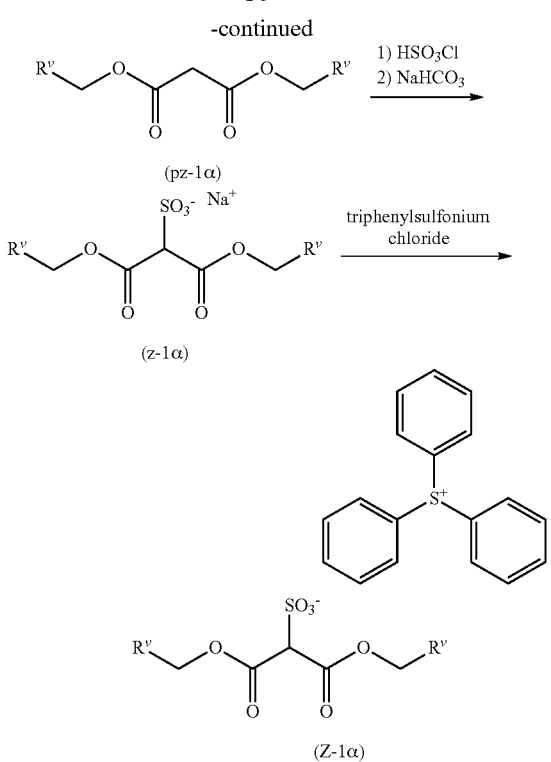

(pz-1α)

(z-1α)

(Z-1α)

In the scheme, RVs are each independently a group corresponding to each of $R^2$ and $R^3$ in the formula (1).

In a solvent such as dichloromethane, in the presence of triethylamine, an alcohol compound is caused to react with a compound represented by the formula (ppz-1α) to produce a diester compound represented by the formula (pz-1α). Next, in the solvent such as dichloromethane, the resultant diester compound is subsequently caused to react with chlorosulfuric acid, and sodium hydrogencarbonate to produce a sodium sulfonate compound represented by the formula (z-1α). Lastly, the sodium sulfonate compound is caused to react with triphenylsulfonium chloride to conduct a salt exchange. In this way, an onium salt compound is yielded which is represented by the formula (Z-1α). Compounds other than the onium salt compound represented by the formula (Z-1α) can also be synthesized in the same way as described above.

The alcohol compound may be any one of a primary alcohol, a secondary alcohol, and a tertiary alcohol. From the viewpoint of a subsequent advance of the sulfonating reaction, a primary alcohol is in particular preferred. Reasons therefor are unclear; however, it is presumed that one of the reasons is that the primary alcohol is relatively small in steric hindrance, so that a nucleophilic reaction for the sulfonation advances easily.

(Solvent)

The radiation-sensitive resin composition contains a solvent. The solvent is not particularly limited as far as the solvent is a solvent in which at least the following can be dissolved or dispersed: the resin, the onium salt compound, and optional ingredients incorporated into the composition if desired, such as an acid diffusion controlling agent.

Examples of the solvent include an alcohol-based solvent, an ether-based solvent, a ketone-based solvent, an amide-based solvent, an ester-based solvent, and a hydrocarbon-based solvent.

Examples of the alcohol-based solvent include:

a monoalcohol-based solvent having a carbon number of 1 to 18, including iso-propanol, 4-methyl-2-pentanol, 3-methoxybutanol, n-hexanol, 2-ethylhexanol, furfuryl alcohol, cyclohexanol, 3,3,5-trimethylcyclohexanol, and diacetone alcohol;

a polyhydric alcohol having a carbon number of 2 to 18, including ethylene glycol, 1,2-propylene glycol, 2-methyl-2,4-pentanediol, 2,5-hexanediol, diethylene glycol, dipropylene glycol, triethylene glycol, and tripropylene glycol; and a partially etherized polyhydric alcohol-based solvent in which a part of hydroxy groups in the polyhydric alcohol-based solvent is etherized.

Examples of the ether-based solvent include:

a dialkyl ether-based solvent, including diethyl ether, dipropyl ether, and dibutyl ether;

a cyclic ether-based solvent, including tetrahydrofuran and tetrahydropyran;

an ether-based solvent having an aromatic ring, including diphenylether and anisole (methyl phenyl ether); and an etherized polyhydric alcohol-based solvent in which a hydroxy group in the polyhydric alcohol-based solvent is etherized.

Examples of the ketone-based solvent include:

a chain ketone-based solvent, including acetone, butanone, and methyl-iso-butyl ketone;

a cyclic ketone-based solvent, including cyclopentanone, cyclohexanone, and methylcyclohexanone; and 2,4-pentanedione, acetonylacetone, and acetophenone.

Examples of the amide-based solvent include:

a cyclic amide-based solvent, including N,N'-dimethyl imidazolidinone and N-methylpyrrolidone; and a chain amide-based solvent, including N-methylformamide, N,N-dimethylformamide, N,N-diethylformamide, acetamide, N-methylacetamide, N,N-dimethylacetamide, and N-methylpropionamide.

Examples of the ester-based solvent include:

a monocarboxylate ester-based solvent, including n-butyl acetate and ethyl lactate;

a partially etherized polyhydric alcohol acetate-based solvent, including diethylene glycol mono-n-butyl ether acetate, propylene glycol monomethyl ether acetate, and dipropylene glycol monomethyl ether acetate;

a lactone-based solvent, including γ-butyrolactone and valerolactone;

a carbonate-based solvent, including diethyl carbonate, ethylene carbonate, and propylene carbonate; and a polyhydric carboxylic acid diester-based solvent, including propylene glycol diacetate, methoxy triglycol acetate, diethyl oxalate, ethyl acetoacetate, ethyl lactate, and diethyl phthalate.

Examples of the hydrocarbon-based solvent include:

an aliphatic hydrocarbon-based solvent, including n-hexane, cyclohexane, and methylcyclohexane;

an aromatic hydrocarbon-based solvent, including benzene, toluene, di-iso-propylbenzene, and n-amylnaphthalene.

Among them, the ester-based solvent or the ketone-based solvent is preferred. The partially etherized polyhydric alcohol acetate-based solvent, the cyclic ketone-based solvent, or the lactone-based solvent is more preferred. Propylene glycol monomethyl ether acetate, cyclohexanone, or γ-butyrolactone is still more preferred. The radiation-sensitive resin composition may include one type of the solvent, or two or more types of the solvents in combination.

(Other Optional Ingredients)

The radiation-sensitive resin composition may also include any other optional ingredient in addition to the ingredients as described above. Examples of the other optional ingredient include an acid diffusion controlling agent, a localization enhancing agent, a surfactant, an alicyclic backbone-containing compound, and a sensitizer. The other optional ingredient may be used alone, or two or more other optional ingredients may be used in combination.

(Acid Diffusion Controlling Agent)

The radiation-sensitive resin composition may include an acid diffusion controlling agent, if needed. The acid diffusion controlling agent has an effect of controlling the diffusion phenomenon in which an acid resulted from the onium salt compound by the exposure is diffused in the resist film, and of inhibiting undesired chemical reaction in the non-exposed part. The acid diffusion controlling agent can also improve the storage stability of the resulting radiation-sensitive resin composition. The acid diffusion controlling agent can further improve the resolution of the resist pattern and prevent from changing the line width of the resist pattern because of the variation of the pulling and placing time, i.e., the time from the exposure to the developing treatment, and therefore provide the radiation-sensitive resin composition having an improved process stability.

Examples of the acid diffusion controlling agent include a compound represented by the following formula (7) (hereinafter, also referred as a "nitrogen-containing compound (I)"); a compound having two nitrogen atoms in one molecule (hereinafter, also referred as a "nitrogen-containing compound (II)"); a compound having three nitrogen atoms in one molecule (hereinafter, also referred as a "nitrogen-containing compound (III)"); a compound having an amide group; a urea compound; and a nitrogen-containing heterocyclic ring compound.

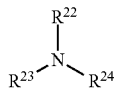

(7)

In the above formula (7), $R^{22}$, $R^{23}$ and $R^{24}$ are each independently a hydrogen atom, a substituted or unsubstituted alkyl group, a substituted or unsubstituted cycloalkyl group, a substituted or unsubstituted aryl group, or a substituted or unsubstituted aralkyl group.

Examples of the nitrogen-containing compound (I) include a monoalkylamine including n-hexylamine; a dialkylamine including di-n-butylamine; a trialkylamine including triethylamine; and an aromatic amine including aniline.

Examples of the nitrogen-containing compound (II) include ethylenediamine and N,N,N',N'-tetramethylethylenediamine.

Examples of the nitrogen-containing compound (III) include a polyamine compound, including polyethyleneimine and polyallylamine; and a polymer including dimethylaminoethylacrylamide.

Examples of the amide-containing compound include formamide, N-methylformamide, N,N-dimethylformamide, acetamide, N-methylacetamide, N,N-dimethylacetamide, propionamide, benzamide, pyrrolidone, and N-methyl pyrrolidone.

Examples of the urea compound include urea, methylurea, 1,1-dimethylurea, 1,3-dimethylurea, 1,1,3,3-tetramethylurea, 1,3-diphenylurea, and tributylthiourea.

Examples of the nitrogen-containing heterocyclic ring compound include pyridines, including pyridine and 2-methylpyridine; morpholines, including N-propylmorpholine and N-(undecylcarbonyloxyethyl)morpholine; pyrazine, and pyrazole.

A compound having an acid-dissociable group may be used as the nitrogen-containing organic compound. Examples of the nitrogen-containing organic compound having an acid-dissociable group include N-t-butoxycarbonylpiperidine, N-t-butoxycarbonylimidazole, N-t-butoxycarbonylbenzimidazole, N-t-butoxycarbonyl-2-phenylbenzimidazole, N-(t-butoxycarbonyl)di-n-octylamine, N-(t-butoxycarbonyl)diethanolamine, N-(t-butoxycarbonyl) dicyclohexylamine, N-(t-butoxycarbonyl)diphenylamine, N-t-butoxycarbonyl-4-hydroxypiperidine, and N-t-amyloxycarbonyl-4-hydroxypiperidine.

The acid diffusion controlling agent may also be a photodegradable base, which generates a weak acid by exposure. The weak acid denotes an acid having an acidity which does not permit the acid-dissociable group represented by the structural unit (I) contained in the resin to be dissociated. The scope of the acid depends on the easiness of the elimination of the used acid-dissociable group. In general, a compound which generates a carboxylic acid by exposure functions as a photodegradable base for a majority of acid-dissociable groups (in other words, the compound causes the acid-dissociable groups not to be dissociated) In contrast, out of compounds which generates a sulfonic acid by exposure, any compound that generates a sulfonic acid weak in acid strength acts, for a resin in which an easily-eliminable acid-dissociable group is used, as an agent which generates an acid for causing this acid-dissociable group to be eliminated. However, for a resin making use of an acid-dissociable group which is not easily eliminated (for example, an acid-dissociable group in which $R^8$ to $R^{10}$ in the formula (2) as used frequently in resists for ArF-exposure are each a chain hydrocarbon group or alicyclic hydrocarbon group), the compound acts as a photodegradable base since an acid to be generated therefrom is low in acid-dissociable group eliminability.

Example of the photodegradable base includes an onium salt compound in which the compound is degraded by the exposure to lose the acid diffusion controlling properties. Examples of the onium salt compound include a sulfonium salt compound represented by the following formula (8-1), and an iodonium salt compound represented by the following formula (8-2).

(8-1)

(8-2)

In the above formula (8-1) and formula (8-2), $J^+$ is a sulfonium cation; and $U^+$ is an iodonium cation. Examples of the sulfonium cation represented by $J^+$ include sulfonium cations represented by the above formulae (X-1) to (X-3). Examples of the iodonium cation represented by $U^+$ include iodonium cations represented by the above formulae (X-4) to (X-5). $E^-$ and $Q^-$ are each independently anion represented by $OH^-$, $R^\alpha$—$COO^-$, and $R^\alpha$—$SO_3^-$. $R^\alpha$ is an alkyl group, an aryl group, or an aralkyl group. A hydrogen atom in the aromatic ring of the aryl group or the aralkyl group represented by $R^\alpha$ may be substituted with a hydroxy group, a fluorine atom-substituted or unsubstituted alkyl group having a carbon number of 1 to 12, or an alkoxy group having a carbon number of 1 to 12.

Examples of the photodegradable base include compounds represented by the following formulae.

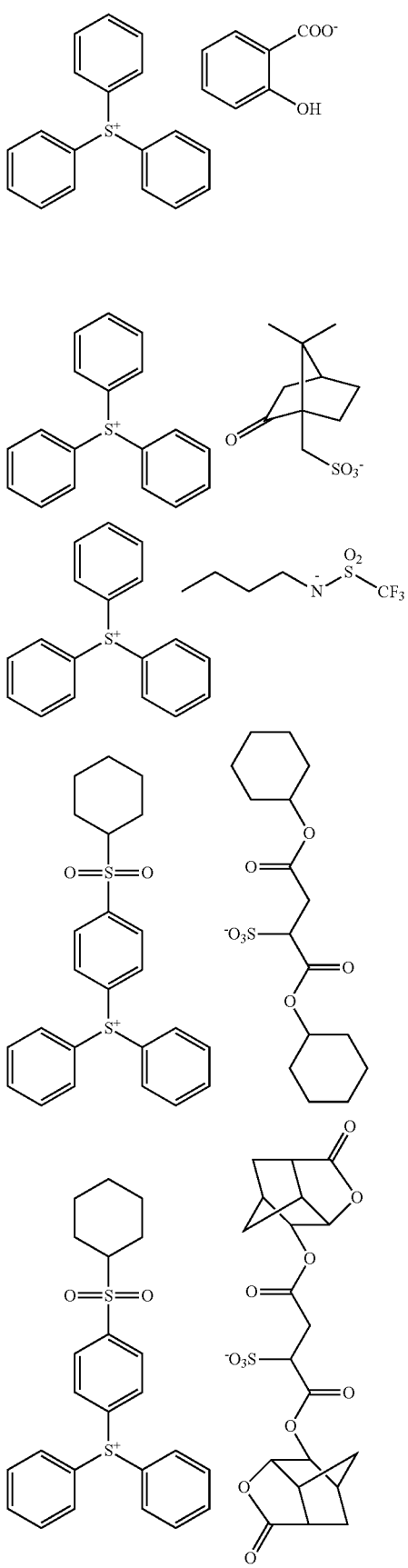
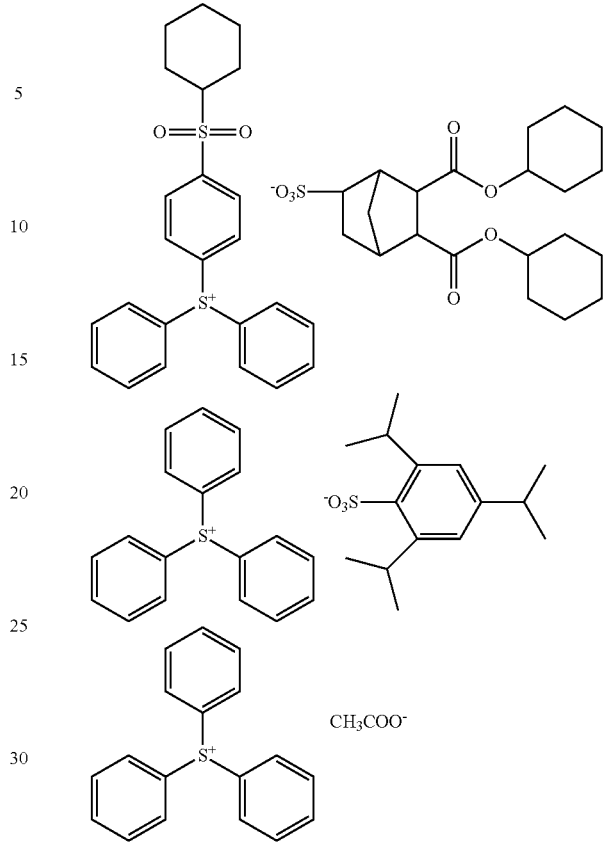

Among them, the photodegradable base is preferably the sulfonium salt, more preferably a triarylsulfonium salt, and further preferably a triphenylsulfonium salicylate or triphenylsulfonium 10-camphorsulfonate.

The lower limit of the content of the acid diffusion controlling agent is preferably 3 parts by mass, more preferably 6 parts by mass, and further preferably 10 parts by mass based on 100 parts by mass of the photodegradable base. The upper limit of the content is preferably 100 parts by mass, more preferably 80 parts by mass, and further preferably 50 parts by mass.

By adjusting the content of the acid diffusion controlling agent within the ranges, the radiation-sensitive resin composition can provide improved lithography properties. The radiation-sensitive resin composition may contain one type of the acid diffusion controlling agent, or two or more acid diffusion controlling agents in combination.

(Localization Enhancing Agent)

The localization enhancing agent has an effect of localizing the high fluorine-containing resin on the surface of the resist film more effectively. The added amount of the high fluorine-containing resin can be decreased compared to the traditionally added amount by including the localization enhancing agent in the radiation-sensitive resin composition. The localization enhancing agent can further prevent from eluting the ingredient of the composition from the resist film to an immersion medium and carry out the immersion exposure at higher speed with a high-speed scan, while maintaining the lithography properties of the radiation-sensitive resin composition. As a result, the hydrophobicity of the surface of the resist film can be improved, resulting in the prevention of the defect due to the immersion, for example, the watermark defect. Example of the compound which may be used as the localization enhancing agent includes a low molecular weight compound having a specific dielectric constant of not less than 30 and not more than 200 and a boiling point of 100° C. or more at 1 atm. Specific examples of the compound include a lactone compound, a carbonate compound, a nitrile compound, and a polyhydric alcohol.

Examples of the lactone compound include γ-butyrolactone, valerolactone, mevaloniclactone, and norbornane lactone.

Examples of the carbonate compound include propylene carbonate, ethylene carbonate, butylene carbonate, and vinylene carbonate.

Example of the nitrile compound includes succinonitrile.

Example of the polyhydric alcohol includes glycerine.

The lower limit of the content of the localization enhancing agent is preferably 10 parts by mass, more preferably 15 parts by mass, further preferably 20 parts by mass, and more further preferably 25 parts by mass based on 100 parts by mass of total resins in the radiation-sensitive resin composition. The upper limit of the content is preferably 300 parts by mass, more preferably 200 parts by mass, further preferably 100 parts by mass, and more further preferably 80 parts by mass. The radiation-sensitive resin composition may include one type of the localization enhancing agent, or two or more types of localization enhancing agents in combination.

(Surfactant)

The surfactant has an effect of improving the coating properties, the striation, and the developability of the composition. Examples of the surfactant include a nonionic surfactant, including polyoxyethylene lauryl ether, polyoxyethylene stearyl ether, polyoxyethylene oleyl ether, polyoxyethylene n-octylphenyl ether, polyoxyethylene n-nonylphenyl ether, polyethylene glycol dilaurate, and polyethylene glycol distearate. Examples of the surfactant which is commercially available include KP341 (manufactured by Shin-Etsu Chemical Co., Ltd.), POLYFLOW No. 75, POLYFLOW No. 95 (all manufactured by Kyoeisha Chemical Co., Ltd.), EFTOP EF301, EFTOP EF303, EFTOP EF352 (all manufactured by Tokem Products), Megafac F171, Megafac F173 (all manufactured by DIC), Fluorad FC430, Fluorad FC431 (all manufactured by Sumitomo 3M Limited.), AsahiGuard AG710, Surflon S-382, Surflon SC-101, Surflon SC-102, Surflon SC-103, SurflonSC-104, Surflon SC-105, SurflonSC-106 (all manufactured by Asahi Glass Co., Ltd.). The content of the surfactant in the radiation-sensitive resin composition is typically not more than 2 parts by mass based on 100 parts by mass of total resins.

(Alicyclic Backbone-Containing Compound)

The alicyclic backbone-containing compound has an effect of improving the dry etching resistance, the shape of the pattern, the adhesiveness between the substrate, and the like.

Examples of the alicyclic backbone-containing compound include:

adamantane derivatives, including 1-adamantane carboxylic acid, 2-adamantanone, and t-butyl 1-adamantane carboxylate;

deoxycholic acid esters, including t-butyl deoxycholate, t-butoxycarbonylmethyl deoxycholate, and 2-ethoxyethyl deoxycholate;

lithocholic acid esters, including t-butyl lithocholate, t-butoxycarbonylmethyl lithocholate, and 2-ethoxyethyl lithocholate; and 3-[2-hydroxy-2,2-bis(trifluoromethyl)ethyl]tetracyclo [4.4.0.1 2,5.17,10]dodecane, and 2-hydroxy-9-methoxycarbonyl-5-oxo-4-oxa-tricyclo[4.2.1.03,7]nonane. The content of the alicyclic backbone-containing compound in the radiation-sensitive resin composition is typically not more than 5 parts by mass based on 100 parts by mass of total resins.

(Sensitizer)

The sensitizer shows an action of increasing the production of the acid, for example, from the onium salt compound, and has an effect of improving the "apparent sensitivity" of the radiation-sensitive resin composition.

Examples of the sensitizer include carbazoles, acetophenones, benzophenones, naphthalenes, phenols, biacetyl, eosin, rose bengal, pyrenes, anthracenes, and phenothiazines. The sensitizer may be used alone, or two or more sensitizers may be used in combination. The content of the sensitizer in the radiation-sensitive resin composition is typically not more than 2 parts by mass based on 100 parts by mass of total resins.

<Method for Preparing Radiation-Sensitive Resin Composition>

For example, the radiation-sensitive resin composition can be prepared by mixing the resin, the onium salt compound, optionally the acid diffusion controlling agent, the high fluorine-containing resin, and the solvent in a predetermined ratio. After mixing, the radiation-sensitive resin composition is preferably filtered, for example, through a membrane filter having a pore size of about 0.05 μm. The solid concentration of the radiation-sensitive resin composition is typically from 0.1% by mass to 50% by mass, preferably from 0.5% by mass to 30% by mass, and more preferably from 1% by mass to 20% by mass.

<Onium Salt Compound>

The onium salt compound is represented by the following (1):

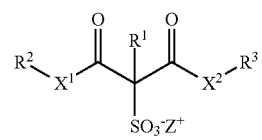

(1)

In the formula (1), $Z^+$ is a monovalent onium cation;

$R^1$ is a hydrogen atom or a monovalent group provided that the monovalent group represented by $R^1$ is not a fluoro group or a monovalent organic group containing a fluorine atom;

$X^1$ and $X^2$ are each independently a single bond, —O—, —S— or —NR'— wherein R' is a hydrogen atom or a monovalent hydrocarbon group, provided that when two R's are present, the two R's are the same or different; and in a case where $X^1$ is —NR'—, $R^2$ is a monovalent organic group or a hydrogen atom, in a case where $X^2$ is —NR'—, $R^3$ is a monovalent organic group or a hydrogen atom, in a case where neither $X^1$ nor $X^2$ is —NR'—, $R^2$ and $R^3$ are each independently a monovalent organic group, optionally, in a case where $X^1$ is —NR'—, $R^2$ is linked to R' in $X^1$ to form a cyclic structure, optionally, in a case where $X^2$ is —NR'—, $R^3$ is linked to R' in $X^2$ to form a cyclic structure, and $R^2$ and $R^3$ are optionally linked with each other to form a cyclic structure.

About the structure, the synthesis method, and other factors of the onium salt compound, the description about the onium salt compound contained in the radiation-sensitive resin composition can be referred to. Thus, description thereabout is omitted herein.

<Method for Forming Resist Pattern>

The method for forming a resist pattern includes:

applying the radiation-sensitive resin composition on a substrate to form a resist film (hereinafter, also referred as a "resist film forming step");

exposing the resist film (hereinafter, also referred as a "exposing step"); and developing the exposed resist film (hereinafter, also referred as a "developing step").

According to the method for forming a resist pattern, the resist pattern can be formed having an improved resolution, the rectangularity of the cross-section shape, LWR properties, depth of focus, MEEF properties, and the shrinkage control of the resist film during PEB. Each step will be described below.

[Resist Film Forming Step]

In this step, the radiation-sensitive resin composition is applied on a substrate to form a resist film. Examples of the substrate on which the resist film is formed include one traditionally known in the art, including a silicon wafer, silicon dioxide, and a wafer coated with aluminum. An organic or inorganic antireflection film may be formed on the substrate, as disclosed in JP-B-06-12452 and JP-A-59-93448. Examples of the applicating method include a rotary coating (spin coating), flow casting, and roll coating. After applicating, a prebake (PB) may be carried out in order to evaporate the solvent in the film, if needed. The temperature of PB is typically from 60° C. to 140° C., and preferably from 80° C. to 120° C. The duration of PB is typically from 5 seconds to 600 seconds, and preferably from 10 seconds to 300 seconds. The thickness of the resist film formed is preferably from 10 nm to 1,000 nm, and more preferably from 10 nm to 500 nm.

When the immersion exposure is carried out, irrespective of presence of a water repellent polymer additive such as the high fluorine-containing resin in the radiation-sensitive resin composition, the formed resist film may have a protective film for the immersion which is not soluble into the immersion liquid on the film in order to prevent a direct contact between the immersion liquid and the resist film. As the protective film for the immersion, a solvent-removable protective film that is removed with a solvent before the developing step (for example, see JP-A-2006-227632); or a developer-removable protective film that is removed during the development of the developing step (for example, see WO2005-069076 and WO2006-035790) may be used. In terms of the throughput, the developer-removable protective film is preferably used.

When the subsequent exposing step is carried out by a radiation having a wavelength of 50 nm or less, the resin having the structural units (I) and (III) as the base resin is preferably used in the composition.

[Exposing Step]

In this step, the resist film formed in the resist film forming step is exposed by irradiating with a radioactive ray through a photomask (optionally through an immersion medium such as water). Examples of the radioactive ray used for the exposure include visible ray, ultraviolet ray, far ultraviolet ray, extreme ultraviolet ray (EUV); an electromagnetic wave including X ray and γ ray; an electron beam; and a charged particle radiation such as α ray. Among them, far ultraviolet ray, an electron beam, or EUV is preferred. ArF excimer laser light (wavelength is 193 nm), KrF excimer laser light (wavelength is 248 nm), an electron beam, or EUV is more preferred. An electron beam or EUV having a wavelength of 50 nm or less which is identified as the next generation exposing technology is further preferred.

When the exposure is carried out by immersion exposure, examples of the immersion liquid include water and fluorine-based inert liquid. The immersion liquid is preferably a liquid which is transparent with respect to the exposing wavelength, and has a minimum temperature factor of the refractive index so that the distortion of the light image reflected on the film becomes minimum. However, when the exposing light source is ArF excimer laser light (wavelength is 193 nm), water is preferably used because of the ease of availability and ease of handling in addition to the above considerations. When water is used, a small proportion of an additive that decreases the surface tension of water and increases the surface activity may be added. Preferably, the additive cannot dissolve the resist film on the wafer and can neglect an influence on an optical coating at an under surface of a lens. The water used is preferably distilled water.

After the exposure, post exposure bake (PEB) is preferably carried out to promote the dissociation of the acid-dissociable group in the resin by the acid generated from the onium salt compound with the exposure in the exposed part of the resist film. The difference of solubility into the developer between the exposed part and the non-exposed part is generated by the PEB. The temperature of PEB is typically from 50° C. to 180° C., and preferably from 80° C. to 130° C. The duration of PEB is typically from 5 seconds to 600 seconds, and preferably from 10 seconds to 300 seconds.

[Developing Step]

In this step, the resist film exposed in the exposing step is developed. By this step, the predetermined resist pattern can be formed. After the development, the resist pattern is washed with a rinse solution such as water or alcohol, and the dried, in general.

Examples of the developer used for the development include, in the alkaline development, an alkaline aqueous solution obtained by dissolving at least one alkaline compound such as sodium hydroxide, potassium hydroxide, sodium carbonate, sodium silicate, sodium metasilicate, ammonia water, ethylamine, n-propylamine, diethylamine, di-n-propylamine, triethylamine, methyldiethylamine, ethyldimethylamine, triethanolamine, tetramethyl ammonium hydroxide (TMAH), pyrrole, piperidine, choline, 1,8-diazabicyclo-[5.4.0]-7-undecene, 1,5-diazabicyclo-[4.3.0]-5-nonene. Among them, an aqueous TMAH solution is preferred, and 2.38% by mass of aqueous TMAH solution is more preferred.

In the case of the development with organic solvent, examples of the solvent include an organic solvent, including a hydrocarbon-based solvent, an ether-based solvent, an ester-based solvent, a ketone-based solvent, and an alcohol-based solvent; and a solvent containing an organic solvent. Examples of the organic solvent include one, two or more solvents listed as the solvent for the radiation-sensitive resin composition. Among them, an ester-based solvent or a ketone-based solvent is preferred. The ester-based solvent is preferably an acetate ester-based solvent, and more preferably n-butyl acetate or amyl acetate. The ketone-based solvent is preferably a chain ketone, and more preferably 2-heptanone. The content of the organic solvent in the developer is preferably not less than 80% by mass, more preferably not less than 90% by mass, further preferably not less than 95% by mass, and particularly preferably not less than 99% by mass. Examples of the ingredient other than the organic solvent in the developer include water and silicone oil.

Examples of the developing method include a method of dipping the substrate in a tank filled with the developer for a given time (dip method); a method of developing by putting and leaving the developer on the surface of the substrate with the surface tension for a given time (paddle method); a method of spraying the developer on the surface of the substrate (spray method); and a method of injecting the developer while scanning an injection nozzle for the developer at a constant rate on the substrate rolling at a constant rate (dynamic dispense method).

EXAMPLES

Hereinafter, the present invention will be described in detail by way of working examples thereof. However, the invention is not limited to the examples, and modifications of the examples are included in the scope of the invention as far as the modifications are not beyond the scope of subject matters thereof. In the working examples, and comparative examples, measurements were made by methods described below.

[Weight-Average Molecular Weight (Mw) and Number-Average Molecular Weight (Mn)]

The Mw and the Mn of each polymer used in the working examples were measured by using GPC columns (two G2000 HXL columns, one G3000 HXL column, and one G4000 HXL column) manufactured by Tosoh Corp., and using gel permeation chromatography (GPC) using a mono-dispersed polystyrene as a standard under the following analysis conditions: flow rate: 1.0 mL/min., elution solvent: tetrahydrofuran, sample concentration: 1.0% by mass, sample injected volume: 100 μL, column temperature: 40° C., and detector: differential refractometer. The dispersity (Mw/Mn) of the polymer was calculated out from results of the measured Mw and Mn.

[$^{13}$C-NMR Analysis]

A machine "JNM-ECX 400" manufactured by JEOL Ltd. was used to make an analysis for gaining the content by proportion (mol %) of each structural unit in each of the polymers, using deuterium chloroform as a measuring solvent.

<Synthesis of Onium Salt Compounds>

Example 1

(Synthesis of Onium Salt Compound (Z-1))

Into a 300-mL round bottom flask were added 16.21 g (142 mmol) of cyclohexanemethanol, 14.86 g (147 mmol) of triethylamine, and 200 g of dichloromethane, and then under a nitrogen atmosphere, these components were stirred at 0° C. Thereto was dropwise added 10 g (71 mmol) of dichloride malonate represented by the formula (ppz-1). The temperature of the system was then raised to room temperature, and the components were stirred for one hour. Thereto was added 60 g of water, and the resultant was subjected to extraction with 100 g of dichloromethane three times. The resultant organic phase was dried over sodium sulfate, and then the solvent was distilled off. The phase was purified by column chromatography to yield 18.3 g (yield: 87%) of a compound (pz-1).

Next, 6 g (20.0 mmol) of the compound (pz-1) and 20 mL of dichloromethane were added to a 100-mL round bottom flask. Under a nitrogen atmosphere, the components were stirred at 0° C. Subsequently, thereto was dropwise added 2.47 g (21.2 mmol) of chloro sulfate, and the components were then stirred for 30 minutes. The components were heated and refluxed for 2 hours. The reaction liquid was concentrated, and then thereto were added a mixed liquid of ethanol and water (ratio (v/v)=¼), and 1.85 g (22 mmol) of sodium hydrogencarbonate. The reaction liquid was stirred for 30 minutes and concentrated to yield a reaction mixture containing a compound (z-1). Subsequently, to the present mixture were added 5.97 g (20 mmol) of triphenylsulfonium chloride (TPSCl), 70 g of dichloromethane, and 30 g of water, and the resultant liquid was stirred for 5 hours. Next, an organic phase was collected from the reaction liquid after the stirring, and washed with water 5 times. The solvent was distilled off from this washed organic phase, and this phase was purified by column chromatography to yield 6.26 g (yield: 49%) of a compound (Z-1).

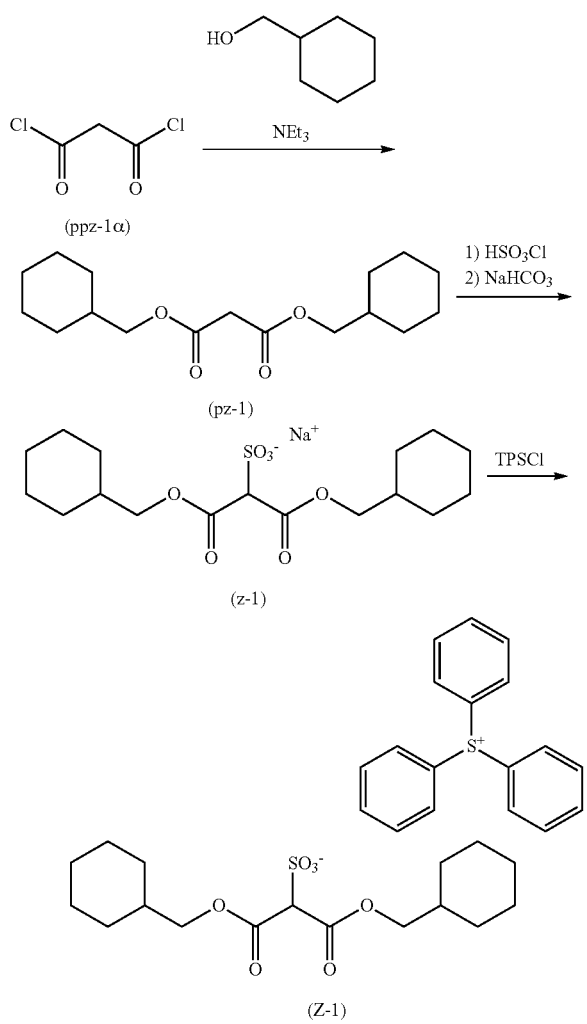

Examples 2 to 16

(Synthesis of Compounds (Z-2) to (Z-16))

Onium salt compounds represented by formulae (Z-2) to (Z-16) illustrated below, respectively, were each synthesized by selecting an appropriate precursor, and selecting the same method as described in Example 1. These are illustrated together with the onium salt compound represented by the formula (Z-1).

(Z-1)
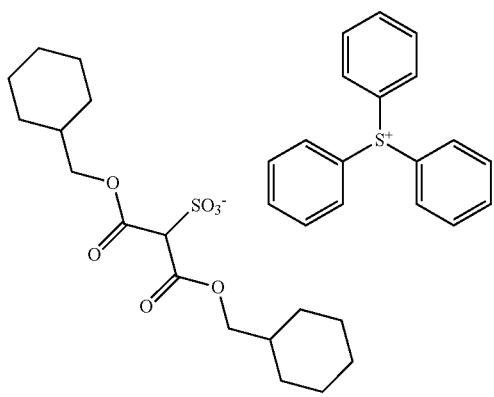
(Z-2)
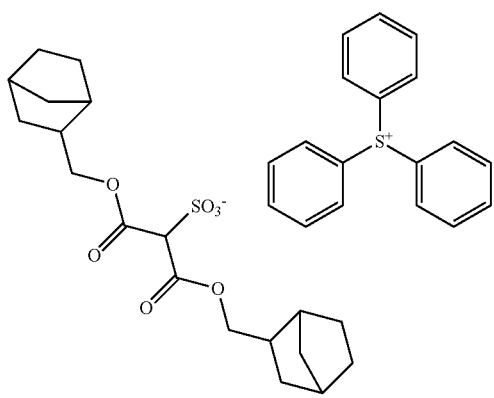
(Z-3)
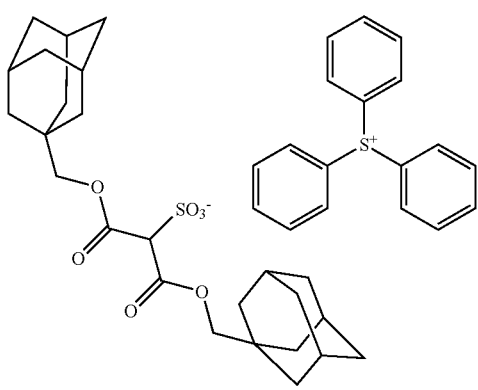
(Z-4)
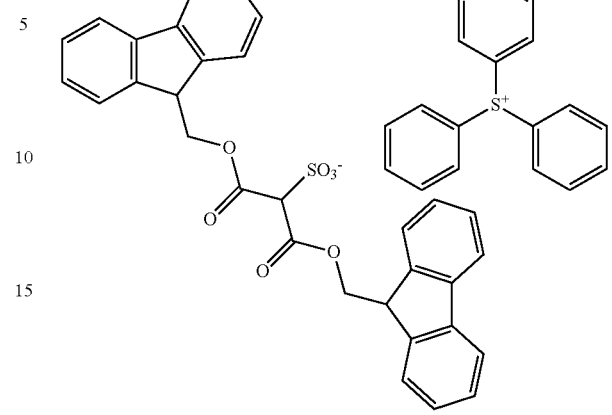
(Z-5)
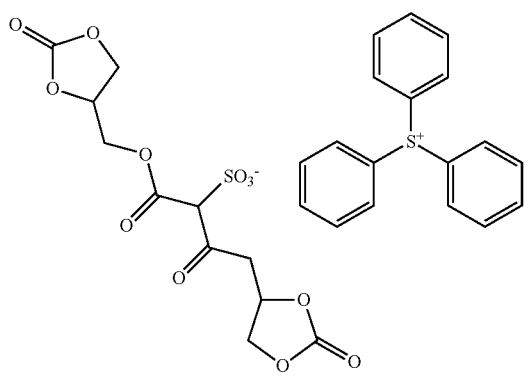
(Z-6)
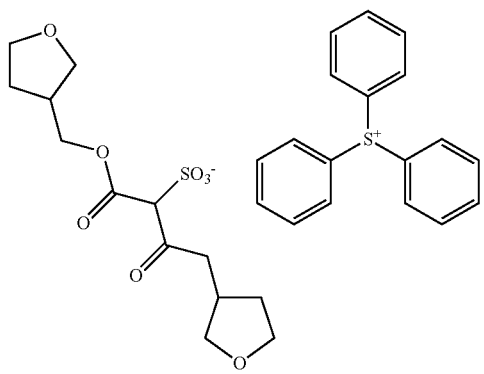
(Z-7)

(Z-8) 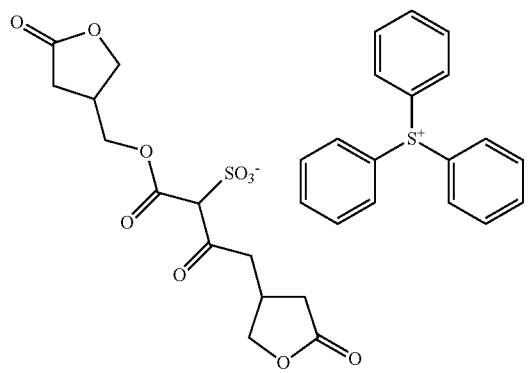
(Z-9) 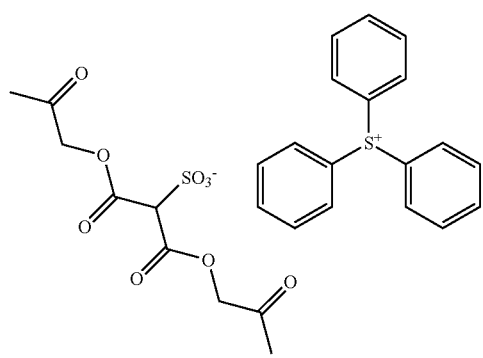
(Z-10) 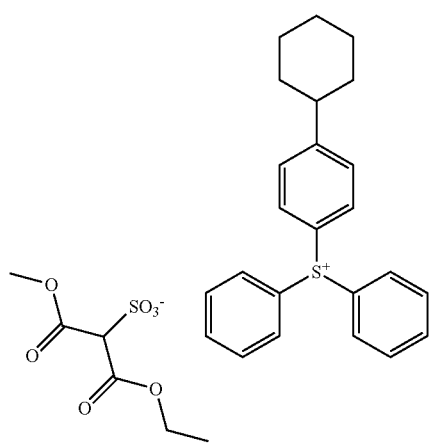
(Z-11) 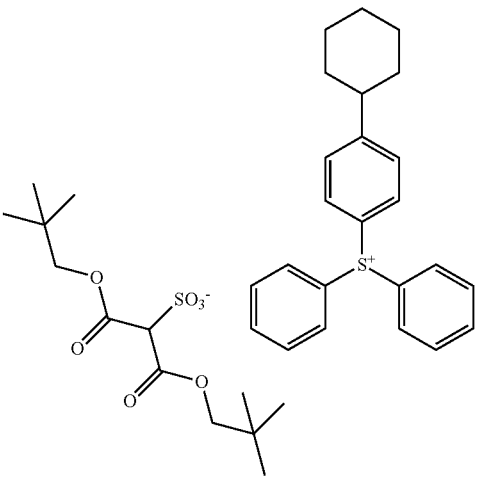
(Z-12) 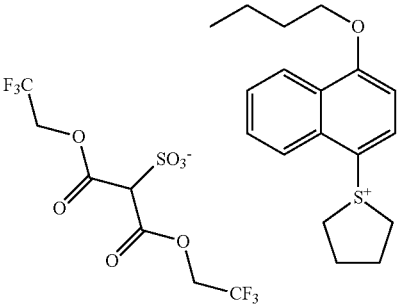
(Z-13) 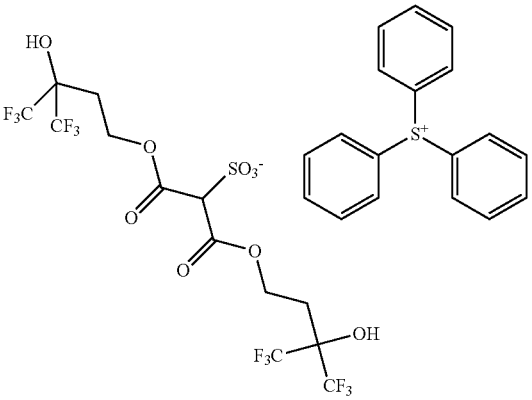
(Z-14) 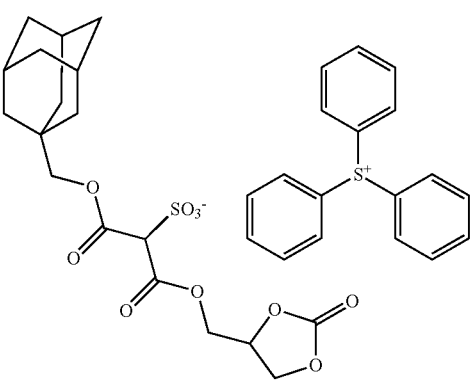

(Z-15)
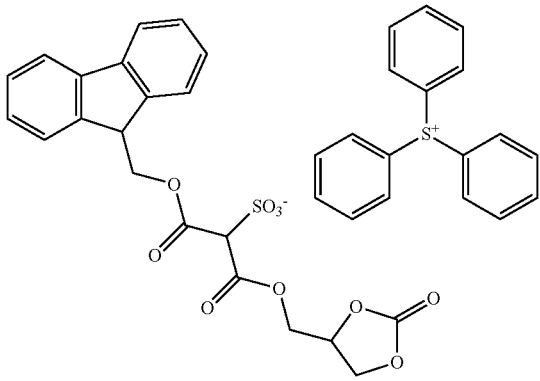
(Z-16)
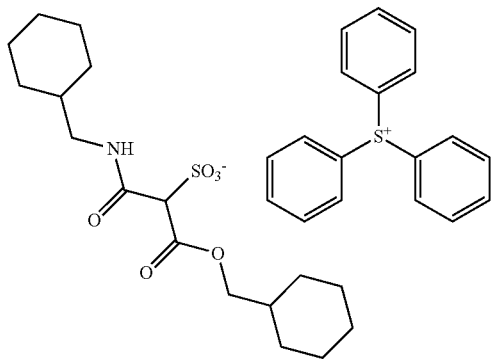
<Synthesis of Base Resins and High-Fluorine-Content Resins>
The following illustrates a monomer used in the synthesis of a resin in each of the working examples and comparative examples.
(M-1)
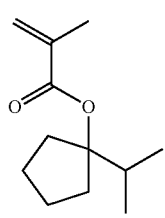
(M-2)
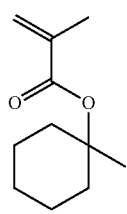
(M-3)
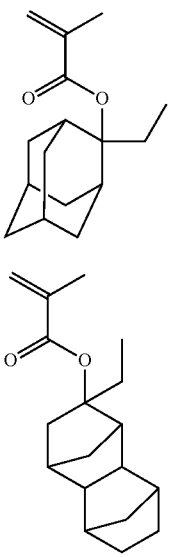
(M-4)
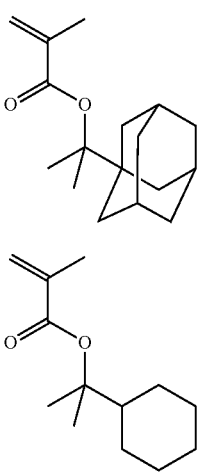
(M-5)
(M-6)
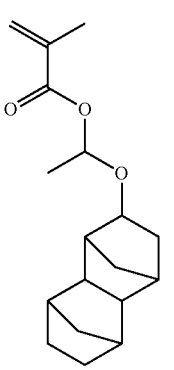
(M-7)
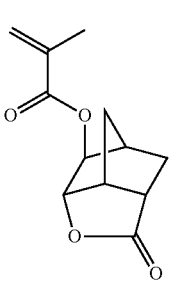
(M-8)

-continued

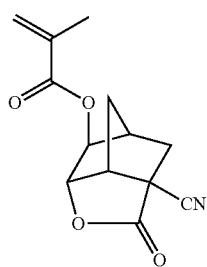
(M-9)

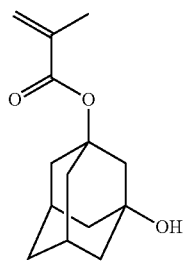
(M-10)

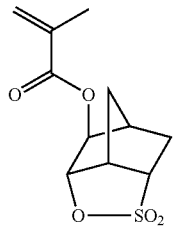
(M-11)

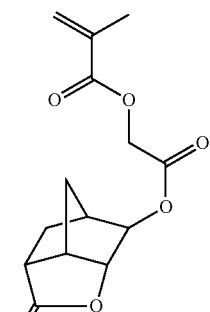
(M-12)

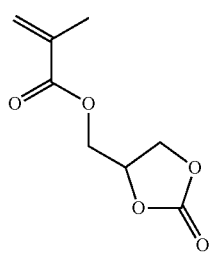
(M-13)

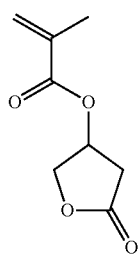
(M-14)

-continued

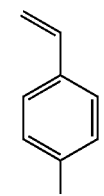
(M-15)

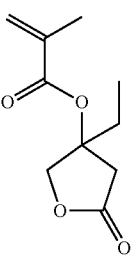
(M-16)

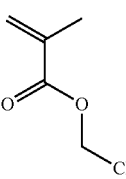
(M-17)

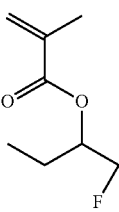
(M-18)

Synthesis Example 1

(Synthesis of Base Resin (A-1))

Into 40 g of 2-butanone were dissolved 9.38 g (50 mol %) of the compound (M-1) and 10.62 g (50 mol %) of the compound (M-8), and then 0.785 g (5 mol % of the whole of the monomers) of azobisisobutyronitrile was further dissolved into the resultant solution to prepare a monomer solution. Next, while 20 g of 2-butanone put into a 200-mL three-necked flask was stirred under a nitrogen atmosphere, the solvent was heated to 80° C. Thereto was dropwise added the prepared monomer solution over 3 hours. After the end of the addition, this reaction liquid was further heated at 80° C. for 3 hours to conduct a polymerization reaction. After the end of the polymerization reaction, the reaction liquid was cooled to room temperature, and then put into 300 g of methanol. The precipitated solid was filtrated to be separated. The filtrated and separated solid was washed with 60 mL of methanol 2 times, and further the resultant solid was filtrated to be separated. Thereafter, the solid was dried at 50° C. under a reduced pressure for 15 hours to yield a base resin (A-1) (yielded amount: 15.8 g, and yield: 78.9%). The Mw of the polymer (A-1) was 6,100, and the Mw/Mn was 1.41. As a result of a $^{13}$C-NMR analysis thereof, in the base resin (A-1), the respective contents by proportion of structural units derived from the compound (M-1) and ones derived from the compound (M-8) were 49.8 mol %, and 50.2 mol %.

Synthesis Examples 2 to 7

(Synthesis of Base Resins (A-2) to (A-7))

Base resins (A-2) to (A-7) were each synthesized in the same way as in Synthesis Example 1 except that a monomer of a species shown in Table 1 described below and a use amount shown therein were used.

Synthesis Example 8

(Synthesis of Base Resin (A-8))

Into 100 g of propylene glycol monomethyl ether were dissolved 45.24 g (50 mol %) of the compound (M-15), 54.76 g (50 mol %) of the compound (M-1), 4.58 g (5 mol % of the whole of the monomers) of azobisisobutyronitrile as an initiator, and 1.14 g of t-dodecylmercaptane, and then the monomers were copolymerized at a reaction temperature kept at 70° C. under a nitrogen atmosphere for 16 hours. After the end of the polymerization reaction, the polymerization solution was dropwise added to 1,000 g of n-hexane to be solidified and purified. To the resultant solid was again added 150 g of propylene glycol monomethyl ether, and further thereto were added 150 g of methanol, 34 g of triethylamine, and 6 g of water. While refluxed at the boiling point, the reaction system was subjected to hydrolysis reaction for 8 hours. After the end of the reaction, the solvent and triethylamine were distilled off under a reduced pressure. The resultant solid was dissolved into 150 g of acetone, and then the resultant was dropwise added to 2,000 g of water to be solidified. The produced solid was filtrated, and dried at 50° C. for 17 hours to yield a white powdery base resin (A-8) (yielded amount: 63.8 g, and yield: 72.3%). The Mw of the base resin (A-8) was 6,400, and the Mw/Mn was 1.72. As a result of a $^{13}$C-NMR analysis thereof, in the base resin (A-8), the respective contents by proportion of p-hydroxystyrene units and structural units derived from the compound (M-1) were 48.8 mol %, and 51.2 mol %.

Synthesis Example 9

(Synthesis of High-Fluorine-Content Resin (D-1))

Into 20 g of 2-butanone were dissolved 5.52 g (20 mol %) of the compound (M-16), 10.18 g (40 mol %) of the compound (M-17), and 14.30 g (40 mol %) of the compound (M-18), and then to the resultant solution was further dissolved 1.16 g (5 mol % of the whole of the monomers) of azobisisobutyronitrile to prepare a monomer solution. Next, while 10 g of 2-butanone put into a 100-mL three-necked flask was stirred under a nitrogen atmosphere, the solvent was heated to 80° C. Thereto was dropwise added the monomer solution over 3 hours. After the end of the addition, the reaction liquid was further heated at 80° C. for 3 hours to conduct a polymerization reaction. After the end of the polymerization reaction, the reaction liquid was cooled to room temperature. The reaction liquid was shifted to a separatory funnel, and then the reaction liquid was uniformly diluted with 45 g of n-hexane. Thereto was then charged 180 g of methanol, and the entire components were mixed with each other. Next, to this mixed liquid was added 9 g of distilled water. Furthermore, this liquid was stirred, and allowed to stand still for 30 minutes. Next, from the mixed liquid, the lower phase was collected. The solvent in the collected lower phase was substituted with propylene glycol monomethyl ether acetate to yield a propylene glycol monomethyl ether acetate solution (yield: 72.0%) containing a polymer (D-1), which was a solid. The Mw of the high-fluorine-content resin (D-1) was 7,300, and the Mw/Mn was 2.00. As a result of a $^{13}$C-NMR analysis thereof, in the high-fluorine-content resin (D-1), the respective contents by proportion of structural units derived from the compound (M-16), the compound (M-17) and the compound (M-18), respectively, were 20.1 mol %, 38.9 mol %, and 41.0 mol %.

<Preparation of Radiation-Sensitive Resin Compositions>

Other acid generators, acid diffusion controlling agents and solvents used for preparing the radiation-sensitive resin compositions in the working examples and the comparative examples are described below.

TABLE 1

| | Monomer giving structural units (I) | | | Monomer giving structural units other than structural units (I) | | | | |
|---|---|---|---|---|---|---|---|---|
| Base resin | Species | Used amount (mol %) | Structural unit content by proportion (mol %) | Species | Used amount (mol %) | Structural unit content by proportion (mol %) | Yield (%) | Mw | Mw/Mn |
| Synthesis Example 1 | A-1 | M-1 | 50 | 49.8 | M-8 | 50 | 50.2 | 78.9 | 6,100 | 1.41 |
| Synthesis Example 2 | A-2 | M-2 | 50 | 50.4 | M-9 | 50 | 49.6 | 79.3 | 6,200 | 1.39 |
| Synthesis Example 3 | A-3 | M-3 | 50 | 48.9 | M-10 | 50 | 51.1 | 82.3 | 6,300 | 1.42 |
| Synthesis Example 4 | A-4 | M-4 | 50 | 49.5 | M-11 | 50 | 50.5 | 81.2 | 6,200 | 1.43 |
| Synthesis Example 5 | A-5 | M-5 | 50 | 49.7 | M-12 | 50 | 50.3 | 73.5 | 6,100 | 1.40 |
| Synthesis Example 6 | A-6 | M-6 | 50 | 50.2 | M-13 | 50 | 49.8 | 70.2 | 6,400 | 1.44 |
| Synthesis Example 7 | A-7 | M-7 | 50 | 49.2 | M-14 | 50 | 50.8 | 67.4 | 6,200 | 1.45 |
| Synthesis Example 8 | A-8 | M-1 | 50 | 51.2 | M-15[a] | 50 | 48.8 | 72.3 | 6,400 | 1.72 |

[a]The units were present as p-hydroxystyrene units in the (A-8).

[Other Acid Generators]

Individual structural formulae are illustrated below.

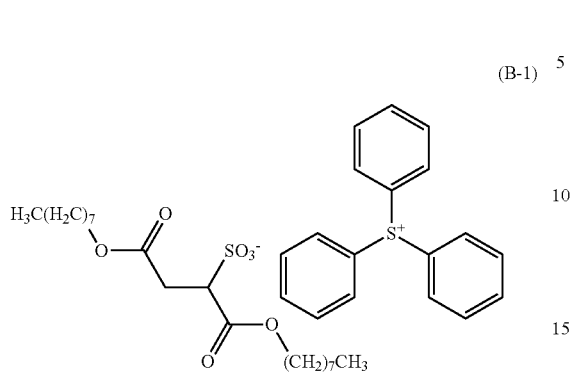
(B-1)

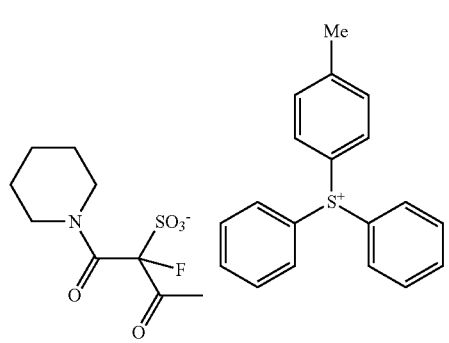
(B-2)

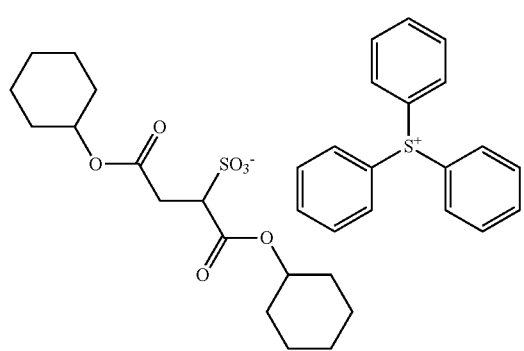
(B-3)

[Acid Diffusion Controlling Agents]

Individual names and structural formulae are described or illustrated below.

C-1: Triphenylsulfonium salicylate,
C-2: Triphenylsulfonium 10-camphorsulfonate, and
C-3: N-(n-undecane-1-ylcarbonyloxyethyl)morpholine.

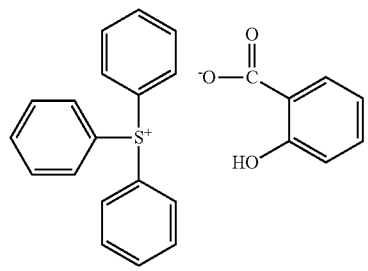
(C-1)

(C-2)

(C-3)

[Solvents]

E-1: Propylene glycol monomethyl ether acetate, and
E-2: Cyclohexanone.

[Uneven Distribution Promoter]

F-1: γ-Butyrolactone.

<Performance Evaluations upon ArF Exposure>

Example 17

(Preparation of Radiation-Sensitive Resin Composition (J-1))

The following were blended with each other and the blend was filtrated through a membrane filter having a pore size of 0.2 m to prepare a radiation-sensitive resin composition (J-1): 100 parts by mass of the base resin (A-1); 7.9 parts by mass of the onium salt compound (Z-1); 1.6 parts by mass of the acid diffusion controlling agent (C-1); 3 parts by mass of the high-fluorine-content resin (D-1); 2,240 parts by mass of the solvent (E-1); 960 parts by mass of the solvent (E-2); and 30 parts by mass of the uneven distribution promoter (F-1).

Examples 18 to 41, and Comparative Examples 1 to 3

(Preparation of Radiation-Sensitive Resin Compositions (J-2) to (J-24), and (CJ-1) to (CJ-3))

Individual radiation-sensitive resin compositions were each prepared in the same way as in Example 17 except that individual components of species shown in Table 2 described below and blended amounts shown therein were used.

TABLE 2

| | Radiation-sensitive resin composition | Base resin Species | Content (parts by mass) | Onium salt compound Species | Content (parts by mass) | Acid diffusion controlling agent Species | Content (parts by mass) | High-fluorine-content resin Species | Content (parts by mass) | Solvent Species | Content (parts by mass) | Uneven distribution promoter Species | Content (parts by mass) |
|---|---|---|---|---|---|---|---|---|---|---|---|---|---|
| Example 17 | J-1 | A-1 | 100 | Z-1 | 7.9 | C-1 | 1.6 | D-1 | 3 | E-1/E-2 | 2240/960 | F-1 | 30 |
| Example 18 | J-2 | A-1 | 100 | Z-2 | 7.9 | C-1 | 1.6 | D-1 | 3 | E-1/E-2 | 2240/960 | F-1 | 30 |
| Example 19 | J-3 | A-1 | 100 | Z-3 | 7.9 | C-1 | 1.6 | D-1 | 3 | E-1/E-2 | 2240/960 | F-1 | 30 |
| Example 20 | J-4 | A-1 | 100 | Z-4 | 7.9 | C-1 | 1.6 | D-1 | 3 | E-1/E-2 | 2240/960 | F-1 | 30 |
| Example 21 | J-5 | A-1 | 100 | Z-5 | 7.9 | C-1 | 1.6 | D-1 | 3 | E-1/E-2 | 2240/960 | F-1 | 30 |
| Example 22 | J-6 | A-1 | 100 | Z-6 | 7.9 | C-1 | 1.6 | D-1 | 3 | E-1/E-2 | 2240/960 | F-1 | 30 |
| Example 23 | J-7 | A-1 | 100 | Z-7 | 7.9 | C-1 | 1.6 | D-1 | 3 | E-1/E-2 | 2240/960 | F-1 | 30 |
| Example 24 | J-8 | A-1 | 100 | Z-8 | 7.9 | C-1 | 1.6 | D-1 | 3 | E-1/E-2 | 2240/960 | F-1 | 30 |
| Example 25 | J-9 | A-1 | 100 | Z-9 | 7.9 | C-1 | 1.6 | D-1 | 3 | E-1/E-2 | 2240/960 | F-1 | 30 |
| Example 26 | J-10 | A-1 | 100 | Z-10 | 7.9 | C-1 | 1.6 | D-1 | 3 | E-1/E-2 | 2240/960 | F-1 | 30 |
| Example 27 | J-11 | A-1 | 100 | Z-11 | 7.9 | C-1 | 1.6 | D-1 | 3 | E-1/E-2 | 2240/960 | F-1 | 30 |
| Example 28 | J-12 | A-1 | 100 | Z-12 | 7.9 | C-1 | 1.6 | D-1 | 3 | E-1/E-2 | 2240/960 | F-1 | 30 |
| Example 29 | J-13 | A-1 | 100 | Z-13 | 7.9 | C-1 | 1.6 | D-1 | 3 | E-1/E-2 | 2240/960 | F-1 | 30 |
| Example 30 | J-14 | A-1 | 100 | Z-14 | 7.9 | C-1 | 1.6 | D-1 | 3 | E-1/E-2 | 2240/960 | F-1 | 30 |
| Example 31 | J-15 | A-1 | 100 | Z-15 | 7.9 | C-1 | 1.6 | D-1 | 3 | E-1/E-2 | 2240/960 | F-1 | 30 |
| Example 32 | J-16 | A-1 | 100 | Z-16 | 7.9 | C-1 | 1.6 | D-1 | 3 | E-1/E-2 | 2240/960 | F-1 | 30 |
| Example 34 | J-17 | A-2 | 100 | Z-1 | 7.9 | C-1 | 1.6 | D-1 | 3 | E-1/E-2 | 2240/960 | F-1 | 30 |
| Example 35 | J-18 | A-3 | 100 | Z-1 | 7.9 | C-1 | 1.6 | D-1 | 3 | E-1/E-2 | 2240/960 | F-1 | 30 |
| Example 36 | J-19 | A-4 | 100 | Z-1 | 7.9 | C-1 | 1.6 | D-1 | 3 | E-1/E-2 | 2240/960 | F-1 | 30 |
| Example 37 | J-20 | A-5 | 100 | Z-1 | 7.9 | C-1 | 1.6 | D-1 | 3 | E-1/E-2 | 2240/960 | F-1 | 30 |
| Example 38 | J-21 | A-6 | 100 | Z-1 | 7.9 | C-1 | 1.6 | D-1 | 3 | E-1/E-2 | 2240/960 | F-1 | 30 |
| Example 39 | J-22 | A-7 | 100 | Z-1 | 7.9 | C-1 | 1.6 | D-1 | 3 | E-1/E-2 | 2240/960 | F-1 | 30 |
| Example 40 | J-23 | A-1 | 100 | Z-1 | 7.9 | C-2 | 1.6 | D-1 | 3 | E-1/E-2 | 2240/960 | F-1 | 30 |
| Example 41 | J-24 | A-1 | 100 | Z-1 | 7.9 | C-3 | 1.6 | D-1 | 3 | E-1/E-2 | 2240/960 | F-1 | 30 |
| Comparative Example 1 | CJ-1 | A-1 | 100 | B-1 | 7.9 | C-1 | 1.6 | D-1 | 3 | E-1/E-2 | 2240/960 | F-1 | 30 |
| Comparative Example 2 | CJ-2 | A-1 | 100 | B-2 | 7.9 | C-1 | 1.6 | D-1 | 3 | E-1/E-2 | 2240/960 | F-1 | 30 |
| Comparative Example 3 | CJ-3 | A-1 | 100 | B-3 | 7.9 | C-1 | 1.6 | D-1 | 3 | E-1/E-2 | 2240/960 | F-1 | 30 |

[Formation (1) of Resist Pattern by ArF Exposure and Alkaline Development]

A spin coater ("CLEAN TRACK ACT 12" manufactured by Tokyo Electron Ltd.) was used to apply a composition for lower-layer antireflective-film formation ("ARC 66" manufactured by Brewer Science, Inc.) onto a surface of a 12-inch silicon wafer, and then the resultant was heated at 205° C. for 60 seconds to form an antireflective film having an average thickness of 105 nm. The spin coater was used to apply, onto this antireflective film, each of the radiation-sensitive resin compositions prepared as described above, and then the resultant was subjected to PB at 90° C. for 60 seconds. Thereafter, the wafer, onto which the radiation-sensitive resin composition was applied, was cooled at 23° C. for 30 seconds to form a resist film having an average thickness of 90 nm. Next, an ArF excimer laser liquid-immersion exposing machine ("NSR-S610C" manufactured by Nikon Corp.) was used to expose this resist film through a 40-nm line-and-space (L/S=1/1) mask pattern under optical conditions of NA=1.3 and dipole (sigma: 0.977/0.782). After the exposure, the resist film was subjected to PEB at 90° C. for 60 seconds. Thereafter, a 2.38%-by-mass TMAH solution in water was used as an alkaline developer to alkaline-develop the resist film. After the development, the resultant was washed with water, and further dried to form a positive type resist pattern. In the formation of this resist pattern, the following exposure value was used as an optimal exposure value: an exposure value at which a line width formed through a mask showing a target dimension of 40 nm and having a 1/1 line-and-space was to be formed in a 1/1 line-and-space having a line width of 40 nm.

[Formation (2) of Resist Pattern by ArF Exposure and Organic Solvent Development]

A negative type resist pattern was formed by the same operations as made in the formation (1) of the resist pattern except that instead of the TMAH solution in water, n-butyl acetate was used to make a development with the organic solvent, and further no washing with water was performed.

Performances of each of the radiation-sensitive resin compositions upon the ArF exposure were evaluated by making measurements described below about the resist pattern. For the measurement of the length of the resist pattern, a scanning electron microscope ("CG-4100" manufactured by Hitachi High-Technologies Corp.) was used.

[LWR Performance]

The scanning electron microscope was used to observe the resist pattern from above the pattern, and the line width thereof was measured at each of optional 50 points of the pattern. From the distribution of the measured values, the 3σ value of the pattern was gained. This was used as the LWR performance (nm) of the pattern. As the LWR performance value is smaller, the performance is better. When the LWR performance value is 4.0 nm or less, the performance can be judged to be "good". When the performance value is more than 4.0 nm, the performance can be judged to be "bad".

[Resolution]

The dimension of the minimum resist pattern resolved at the optimal exposure value was measured. This measurement result was defined as the resolution value (nm). As the resolution value is smaller, the resolution is better. When the resolution value is 34 nm or less, the resolution can be judged to be "good". When the resolution value is more than 34 nm, the resolution can be judged to be "bad".

[Rectangle-Property of Sectional Shape]

The shape of a cross section of the resist pattern resolved at the optimal exposure value was observed, and measurements were made about the line width Lb of the resist pattern at the middle in the height direction of the pattern, and the line width La thereof at the top therein. The ratio of La to Lb was defined as the rectangle-property of the sectional shape. About the rectangle-property of the sectional shape, when this ratio is 0.9 or more and 1.1 or less, this property can be judged to be "good", and when the ratio is out of this range, the property can be judged to be "bad".

[Focal Depth]

About the resist pattern resolved at the optimal exposure value, the dimension thereof was observed while the focus was changed in the depth direction. In this way, a margin in the depth direction was measured, this margin permitting the pattern dimension to be within 90 to 110% of a standard of the dimension without generating any bridge or residue. This measurement result was defined as the focal depth [nm] of the pattern. As the focal depth value is larger, the result thereof is better. When the focal depth is 60 nm or more, this property can be judged to be "good", and when the depth is more than 60 nm, the property can be judged to be "bad".

[MEEF Performance]

At the optimal exposure value, measurements were made about the respective line widths of the resist pattern that were resolved, respectively, through masks having five sizes (38.0-nm in line/80-nm in pitch, 39.0-nm in line/80-nm in pitch, 40.0-nm in line/80-nm in pitch, 41.0-nm in line/80-nm in pitch, and 42.0-nm in line/80-nm in pitch). The resultant values were plotted in a graph having a transverse axis as the mask size, and a vertical axis as the line width formed through the masks having the respective sizes. The inclination of an approximation straight line calculated out by a least squares method was gained, and this inclination was defined as the MEEF performance of the resist pattern. As the MEEF performance value is smaller, the result thereof is better. When the MEEF performance value is 4.0 or less, this performance can be judged to be "good", and when the performance value is more than 4.0, the performance can be judged to be "bad".

<Evaluation of Membrane Shrinkage Restraining Performance>

A spin coater ("CLEAN TRACK ACT 12" manufactured by Tokyo Electron Ltd.) was used to apply a composition for lower-layer antireflective-film formation ("ARC 66" manufactured by Brewer Science, Inc.) onto a surface of a 12-inch silicon wafer, and then the resultant was heated at 205° C. for 60 seconds to form an antireflective film having an average thickness of 105 nm. The spin coater was used to apply, onto this antireflective film, each of the radiation-sensitive resin compositions prepared as described above, and then the resultant was subjected to PB at 90° C. for 60 seconds. Thereafter, the PB-subjected silicon wafer was cooled at 23° C. for 30 seconds to form a resist film having an average thickness of 90 nm. Next, an ArF excimer laser liquid-immersion exposing machine ("NSR-S610C" manufactured by Nikon Corp.) was used to expose the entire outer surface of this resist film at 70 mJ. Thereafter, the thickness of the film was measured to gain the film thickness A before PEB. Subsequently, the resist film after the entire-surface exposure was subjected to PEB at 90° C. for 60 seconds. Thereafter, the film thickness thereof was again measured to gain the film thickness B after the PEB. From the measured results, a value of $[100\times\{(A-B)/A\}]$ (%) was gained. This value was defined as the film-shrinkage-restraining performance (%). As the film-shrinkage-restraining performance value is smaller, the performance is better. When the film-shrinkage-restraining performance value is 14% or less, this performance can be judged to be "good", and when the performance value is more than 14%, the performance can be judged to be "bad".

In Table 3 are shown the evaluation results of the performances of each of the radiation-sensitive resin compositions at the ArF exposure time, and the evaluation result of the film-shrinkage-restraining performance of the composition.

TABLE 3

| | Radiation-sensitive resin composition | Alkaline development | | | | | Organic solvent development | | | | | Film-shrinkage-restraining performance (%) |
|---|---|---|---|---|---|---|---|---|---|---|---|---|
| | | LWR performance (nm) | Resolution (nm) | Sectional-shape rectangle-property | Focal depth (nm) | MEEF performance | LWR performance (nm) | Resolution (nm) | Sectional-shape rectangle-property | Focal depth (nm) | MEEF performance | |
| Example 17 | J-1 | 3.15 | 32 | 1.03 | 90 | 3.39 | 3.35 | 32 | 1.01 | 80 | 3.42 | 12 |
| Example 18 | J-2 | 3.09 | 31 | 1.00 | 80 | 3.40 | 3.31 | 32 | 0.99 | 70 | 3.39 | 11 |
| Example 19 | J-3 | 3.05 | 30 | 1.01 | 70 | 3.36 | 3.29 | 33 | 0.99 | 70 | 3.38 | 10 |
| Example 20 | J-4 | 3.12 | 31 | 1.05 | 80 | 3.31 | 3.25 | 32 | 0.97 | 70 | 3.37 | 10 |
| Example 21 | J-5 | 3.17 | 31 | 0.98 | 80 | 3.30 | 3.31 | 31 | 1.02 | 90 | 3.45 | 11 |
| Example 22 | J-6 | 3.21 | 32 | 0.97 | 80 | 3.31 | 3.35 | 32 | 0.98 | 80 | 3.46 | 12 |
| Example 23 | J-7 | 3.18 | 32 | 0.99 | 80 | 3.35 | 3.34 | 31 | 0.99 | 80 | 3.41 | 11 |
| Example 24 | J-8 | 3.19 | 31 | 0.97 | 80 | 3.36 | 3.39 | 32 | 1.02 | 70 | 3.49 | 12 |
| Example 25 | J-9 | 3.24 | 32 | 0.98 | 80 | 3.41 | 3.38 | 32 | 0.96 | 70 | 3.50 | 13 |
| Example 26 | J-10 | 3.32 | 34 | 0.94 | 60 | 3.52 | 3.49 | 33 | 1.06 | 70 | 3.55 | 13 |
| Example 27 | J-11 | 3.28 | 33 | 0.95 | 70 | 3.54 | 3.51 | 33 | 1.05 | 60 | 3.59 | 13 |
| Example 28 | J-12 | 3.33 | 33 | 0.95 | 70 | 3.52 | 3.48 | 34 | 1.04 | 70 | 3.51 | 13 |
| Example 29 | J-13 | 3.29 | 33 | 0.96 | 70 | 3.49 | 3.44 | 33 | 1.07 | 60 | 3.59 | 12 |
| Example 30 | J-14 | 3.16 | 31 | 1.00 | 80 | 3.31 | 3.25 | 32 | 1.00 | 80 | 3.43 | 12 |
| Example 31 | J-15 | 3.18 | 31 | 1.02 | 80 | 3.43 | 3.31 | 31 | 1.01 | 80 | 3.39 | 12 |
| Example 32 | J-16 | 3.32 | 32 | 0.96 | 60 | 3.39 | 3.39 | 33 | 0.98 | 70 | 3.37 | 11 |
| Example 34 | J-17 | 3.17 | 32 | 1.03 | 80 | 3.32 | 3.39 | 32 | 1.02 | 70 | 3.41 | 11 |
| Example 35 | J-18 | 3.21 | 31 | 1.04 | 80 | 3.36 | 3.31 | 31 | 0.99 | 80 | 3.48 | 12 |
| Example 36 | J-19 | 3.15 | 31 | 1.01 | 90 | 3.39 | 3.40 | 32 | 0.98 | 80 | 3.42 | 11 |
| Example 37 | J-20 | 3.22 | 32 | 1.02 | 80 | 3.33 | 3.33 | 30 | 0.99 | 80 | 3.49 | 10 |
| Example 38 | J-21 | 3.24 | 31 | 1.01 | 80 | 3.33 | 3.31 | 32 | 1.04 | 70 | 3.46 | 12 |

TABLE 3-continued

|  | Radiation-sensitive resin composition | Alkaline development | | | | | Organic solvent development | | | | | Film-shrinkage-restraining performance (%) |
|---|---|---|---|---|---|---|---|---|---|---|---|---|
|  |  | LWR performance (nm) | Resolution (nm) | Sectional-shape rectangle-property | Focal depth (nm) | MEEF performance | LWR performance (nm) | Resolution (nm) | Sectional-shape rectangle-property | Focal depth (nm) | MEEF performance |  |
| Example 39 | J-22 | 3.19 | 30 | 1.00 | 80 | 3.38 | 3.49 | 33 | 1.03 | 70 | 3.41 | U. |
| Example 40 | J-23 | 3.23 | 32 | 1.01 | 90 | 3.34 | 3.41 | 33 | 1.02 | 90 | 3.45 | 12 |
| Example 41 | J-24 | 3.35 | 33 | 1.00 | 80 | 3.49 | 3.45 | 33 | 1.01 | 80 | 3.49 | 13 |
| Comparative Example 1 | CJ-1 | 4.24 | 38 | 0.86 | 40 | 4.21 | 4.54 | 38 | 1.13 | 40 | 4.44 | 15 |
| Comparative Example 2 | CJ-2 | 4.09 | 37 | 0.89 | 40 | 4.24 | 4.61 | 39 | 1.15 | 30 | 4.52 | 17 |
| Comparative Example 3 | CJ-3 | 4.29 | 40 | 0.79 | 40 | 4.24 | 4.57 | 39 | 1.13 | 30 | 4.79 | 16 |

<Performance Evaluation upon Electron Beam Exposure>

Example 42

(Preparation of Radiation-Sensitive Resin Composition (J-25))

The following were blended with each other and the blend was filtrated through a membrane filter having a pore size of 0.2 μm to prepare a radiation-sensitive resin composition (J-25): 100 parts by mass of the base resin (A-8); 20 parts by mass of the onium salt compound (Z-1); 3.2 parts by mass of the acid diffusion controlling agent (C-1); 3 parts by mass of the high-fluorine-content resin (D-1); and 4,280 parts by mass of the solvent (E-1) and 1,830 parts by mass of the solvent (E-2).

Examples 43 and 44, and Comparative Examples 4 to 6

(Preparation of Radiation-Sensitive Resin Compositions (J-26) and (J-27), and (CJ-4) to (CJ-6))

Individual radiation-sensitive resin compositions were each prepared in the same way as in Example 42 except that individual components of species shown in Table 4 described below and blended amounts shown therein were used.

[Formation (3) of Resist Pattern by Electron Beam Exposure and Alkaline Development]

A spin coater ("CLEAN TRACK ACT 8" manufactured by Tokyo Electron Ltd.) was used to apply each of the radiation-sensitive resin compositions shown in Table 4 onto a surface of an 8-inch silicon wafer, and then the resultant was heated at 90° C. for 60 seconds to perform PB. Thereafter, the silicon wafer was cooled at 23° C. for 30 seconds to form a resist film having an average thickness of 50 nm. Next, a simple-type electron beam image-drawing device ("HL 800D" manufactured by Hitachi, Ltd.; power: 50 keV, and current density: 5.0 A/cm$^2$) was used to radiate an electron beam onto the resist film. After the radiation, the resist film was subjected to PEB at 130° C. for 60 seconds. Thereafter, a 2.38%-by-mass TMAH solution in water was used as an alkaline developer to develop the resist film at 23° C. for 30 seconds, and then the resultant was washed with water and further dried to form a positive type resist pattern.

[Optimal Exposure Value]

The scanning electron microscope was used to observe the resist pattern from above the pattern. An exposure value at which the line width was turned to give a 100-nm line-and-space pattern was defined as an optimal exposure value for the resist (that is, the sensitivity thereof).

[LWR Performance]

The scanning electron microscope was used to observe the resist pattern formed as described above, in which the line width was 100 nm (L/S=1/1), from above the pattern, and the line width thereof was measured at each of 50 optional points of the pattern. From the distribution of the measured values, the 3a value of the pattern was gained. This was used as the LWR performance (nm) of the pattern. As the LWR performance value is smaller, a variation of the pattern in line width is smaller to give a better result. When the LWR performance value is 20 nm or less, the perfor-

TABLE 4

| Radiation-sensitive resin composition | Base resin | | Onium salt compound | | Acid diffusion controlling agent | | High-fluorine-content resin | | Solvent | |
|---|---|---|---|---|---|---|---|---|---|---|
|  | Species | Content (parts by mass) | Species | Content (parts by mass) | Species | Content (parts by mass) | Species | Content (parts by mass) | Species | Content (parts by mass) |
| Example 42 | J-25 | A-8 | 100 | Z-1 | 20 | C-1 | 3.2 | D-1 | 3 | E-1/E-2 | 4280/1830 |
| Example 43 | J-26 | A-8 | 100 | Z-10 | 20 | C-1 | 3.2 | D-1 | 3 | E-1/E-2 | 4280/1830 |
| Example 44 | J-27 | A-8 | 100 | Z-16 | 20 | C-1 | 3.2 | D-1 | 3 | E-1/E-2 | 4280/1830 |
| Comparative Example 4 | CJ-4 | A-8 | 100 | B-1 | 20 | C-1 | 3.2 | D-1 | 3 | E-1/E-2 | 4280/1830 |
| Comparative Example 5 | CJ-5 | A-8 | 100 | B-2 | 20 | C-1 | 3.2 | D-1 | 3 | E-1/E-2 | 4280/1830 |
| Comparative Example 6 | CJ-6 | A-8 | 100 | B-3 | 20 | C-1 | 3.2 | D-1 | 3 | E-1/E-2 | 4280/1830 | mance can be judged to be "good". When the performance value is more than 20 nm, the performance can be judged to be "bad".

TABLE 5

| | Radiation-sensitive resin composition | Alkaline development | |
|---|---|---|---|
| | | Sensitivity ($\mu C/cm^2$) | LWR performance (nm) |
| Example 42 | J-25 | 79 | 14 |
| Example 43 | J-26 | 75 | 16 |
| Example 44 | J-27 | 89 | 17 |
| Comparative Example 4 | CJ-4 | 125 | 26 |
| Comparative Example 5 | CJ-5 | 119 | 23 |
| Comparative Example 6 | CJ-6 | 129 | 27 |

As shown in Tables 3 and 5, the radiation-sensitive resin composition in each of the working examples gave results good in all of LWR performance, resolution, sectional-shape rectangle-property, focal depth, MEEF performance and film-shrinkage-restraining performance when ArF exposure was conducted, and further gave results good in sensitivity and LWR performance when the electron beam was conducted. It is therefore judged that the radiation-sensitive resin composition gives results excellent in all of LWR performance, resolution, sectional-shape rectangle-property, focal depth, MEEF performance and film-shrinkage-restraining performance. In contrast, the radiation-sensitive resin composition of each of the comparative examples gave results bad in at least one or more of these performances. It is generally known that electron beam exposure gives substantially the same tendency as EUV exposure. It is therefore presumed that the radiation-sensitive resin compositions of the working examples also give results excellent in sensitivity and LWR performance when exposed to EUV.

The radiation-sensitive resin composition and the resist-pattern-forming method of the embodiments of the present invention make it possible to form a resist pattern small in LWR, high in resolution and excellent in sectional-shape rectangle-property while exhibiting excellent focal depth, MEEF performance and film-shrinkage-restraining performance. The radiation-sensitive acid generator and the compound of the embodiments of the present invention are usable suitably for a component of a radiation-sensitive resin composition. The method for producing the compound in the embodiment of the present invention makes it possible to give this compound easily and surely. Accordingly, these techniques are usable suitably for producing semiconductor devices expected to be increasingly made finer hereafter.

Obviously, numerous modifications and variations of the present invention are possible in light of the above teachings. It is therefore to be understood that within the scope of the appended claims, the invention may be practiced otherwise than as specifically described herein.

What is claimed is:

1. A radiation-sensitive resin composition, comprising:
   a solvent;
   a resin comprising a structural unit having an acid-dissociable group; and
   an onium salt compound of formula (1),

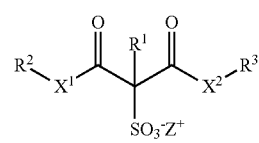

(1)

wherein:
Z$^+$ is a monovalent onium cation;
R$^1$ is a hydrogen atom or a monovalent group provided that the monovalent group represented by R$^1$ is not a fluoro group or a monovalent organic group including a fluorine atom;
X$^1$ and X$^2$ are each independently a single bond, —O—, —S— or —NR'— where R' is a hydrogen atom or a monovalent hydrocarbon group, provided that when two R's are present, the two R's are the same or different;
R$^2$ includes a methylene group directly bonded to X$^1$ and a cyclic structure directly bonded the methylene group; and
R$^3$ includes a methylene group directly bonded to X$^2$ and a cyclic structure directly bonded the methylene group.

2. The radiation-sensitive resin composition according to claim 1, wherein each of R$^2$ and R$^3$ comprises the cyclic structure selected from the group consisting of a lactone structure, a cyclic carbonate structure, a cyclic acetal structure, a cyclic ether structure and a sultone structure.

3. The radiation-sensitive resin composition according to claim 1, wherein the cyclic structure of at least one of R$^2$ and R$^3$ is alicyclic hydrocarbon group.

4. The radiation-sensitive resin composition according to claim 1, wherein at least one of R$^2$ and R$^3$ comprises the cyclic structure selected from the group consisting of a lactone structure, a cyclic carbonate structure, a cyclic acetal structure, a cyclic ether structure and a sultone structure.

5. The radiation-sensitive resin composition according to claim 1, wherein the cyclic structure of at least one of R$^2$ and R$^3$ is aromatic hydrocarbon group.

6. The radiation-sensitive resin composition according to claim 1, wherein the cyclic structure of each of R$^2$ and R$^3$ is an aromatic hydrocarbon group.

7. The radiation-sensitive resin composition according to claim 1, wherein the monovalent onium cation is a sulfonium cation or an iodonium cation.

8. The radiation-sensitive resin composition according to claim 1, wherein the radiation-sensitive resin composition forms a resist pattern by exposure to a radioactive ray having a wavelength of 50 nm or less.

9. The radiation-sensitive resin composition according to claim 1, wherein each of R$^2$ and R$^3$ is independently selected from the group consisting of structures,

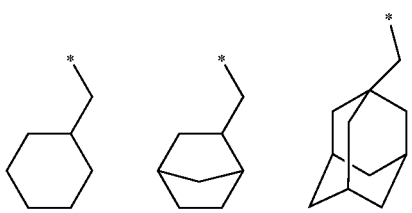

-continued
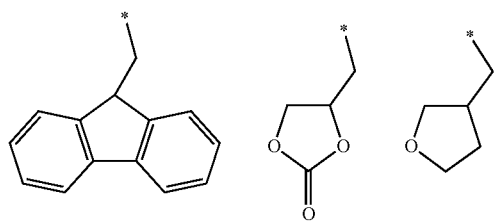
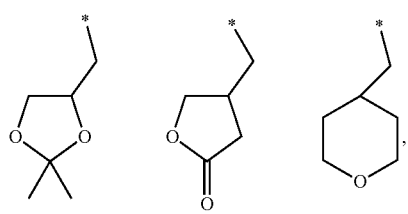
where each * is a hand bonding to $X^1$ or $X^2$.
10. The radiation-sensitive resin composition according to claim 1, wherein each of $R^2$ and $R^3$ is independently selected from the group consisting of Structures (1-1), (1-2), (1-3), (1-4), (1-5), (1-6), (1-7), (1-8), (1-14), (1-15), (1-16), (1-17), (1-18), (1-19), (1-20), (1-21), (1-22), (1-23) and (1-24),
(1-1)
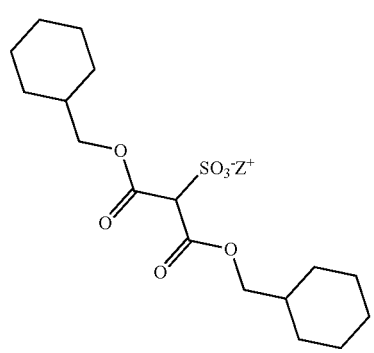
(1-2)
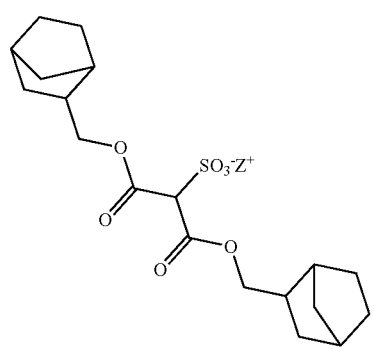
-continued
(1-3)
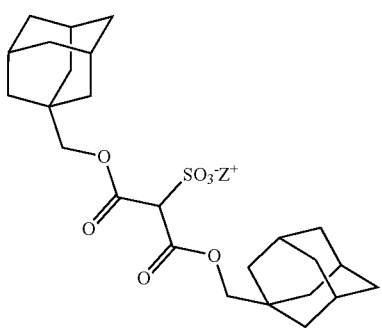
(1-4)
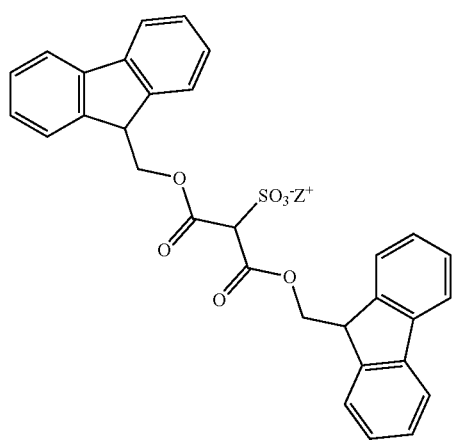
(1-5)
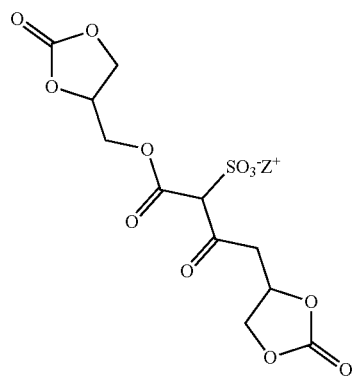
(1-6)
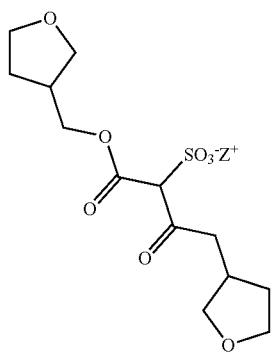

(1-7)
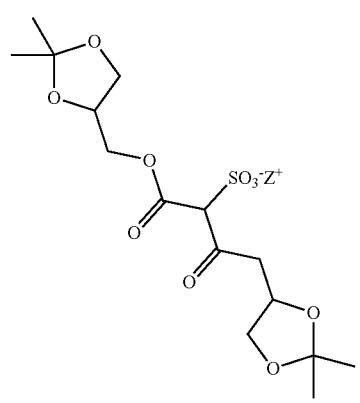
(1-8)
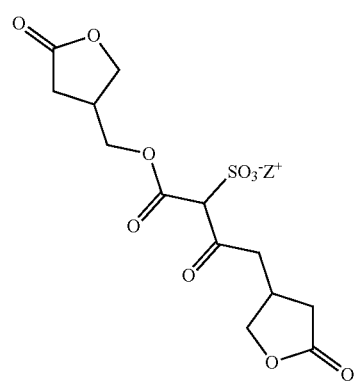
(1-14)
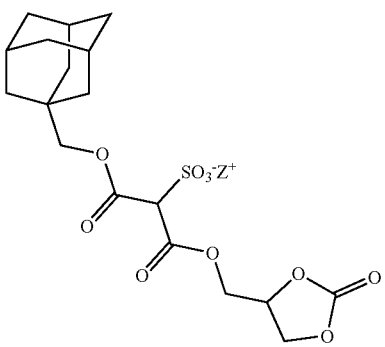
(1-15)
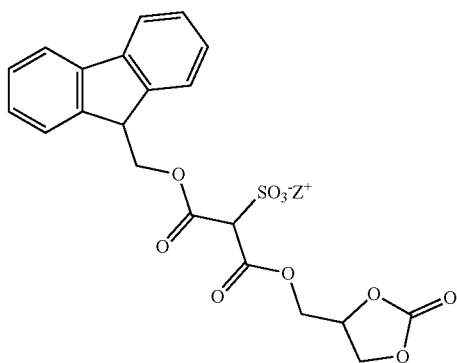
(1-16)
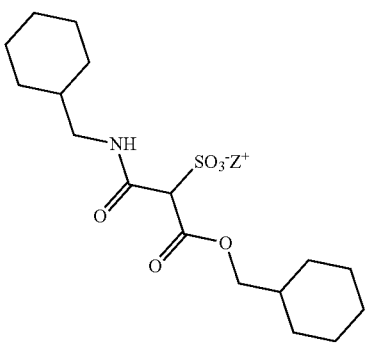
(1-17)
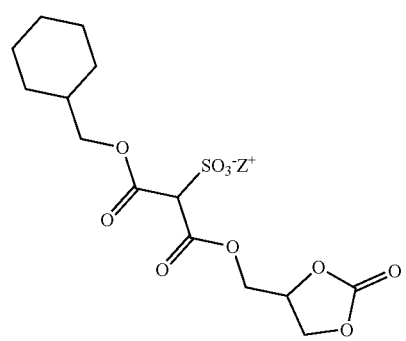
(1-18)
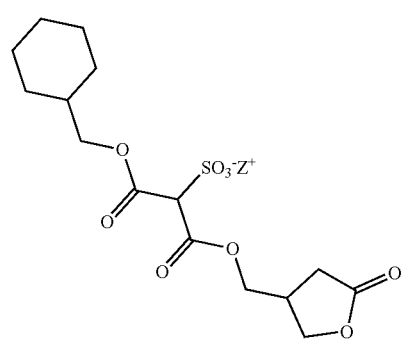
(1-19)
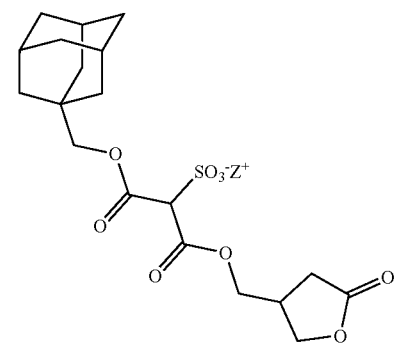

-continued (1-20)
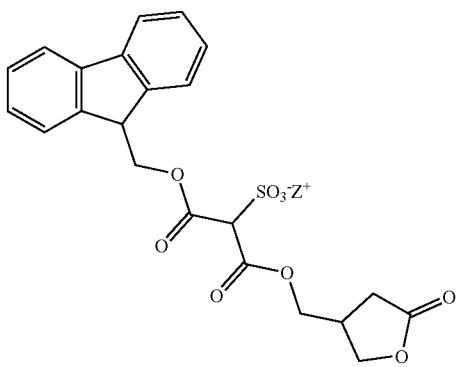

(1-21)
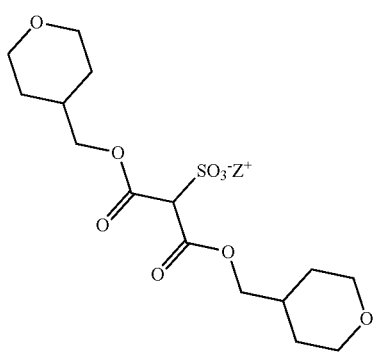

(1-22)
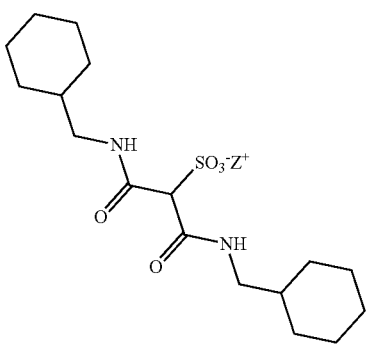

(1-23)
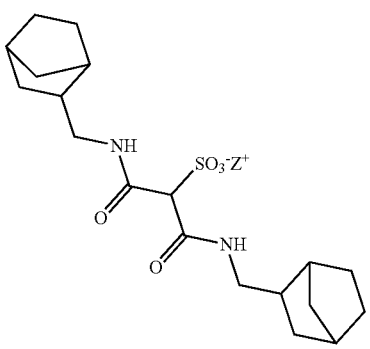

-continued (1-24)
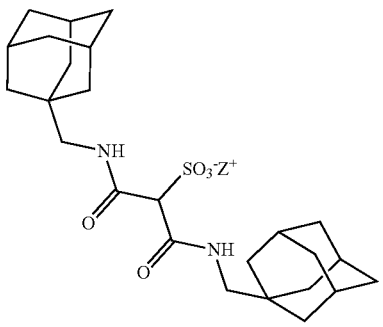

11. An onium salt compound of formula, (1)
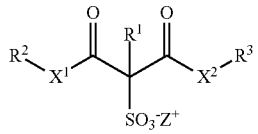

wherein:
$Z^+$ is a monovalent onium cation;
$R^1$ is a hydrogen atom or a monovalent group provided that the monovalent group of $R^1$ is not a fluoro group or a monovalent organic group including a fluorine atom;
$X^1$ and $X^2$ are each independently a single bond, —O—, —S— or —NR' where R' is a hydrogen atom or a monovalent hydrocarbon group, provided that when two R's are present, the two R's are the same or different;
$R^2$ includes a methylene group directly bonded to $X^1$ and a cyclic structure directly bonded the methylene group; and
$R^3$ includes a methylene group directly bonded to $X^2$ and a cyclic structure directly bonded the methylene group.

12. A method for forming a resist pattern, comprising:
applying the radiation-sensitive resin composition of claim 1 on a substrate to form a resist film;
exposing the resist film formed on the substrate; and
developing the resist film after the exposing of the resist film.

13. The method according to claim 12, wherein the exposing comprises exposing the resist film formed on the substrate to a radioactive ray having a wavelength of 50 nm or less.

14. The method according to claim 12, wherein each of $R^2$ and $R^3$ comprises the cyclic structure selected from the group consisting of a lactone structure, a cyclic carbonate structure, a cyclic acetal structure, a cyclic ether structure and a sultone structure.

15. The method according to claim 12, wherein the cyclic structure of at least one of $R^2$ and $R^3$ is an alicyclic hydrocarbon group.

16. The method according to claim 12, wherein at least one of $R^2$ and $R^3$ comprises the cyclic structure selected from the group consisting of a lactone structure, a cyclic carbonate structure, a cyclic acetal structure, a cyclic ether structure and a sultone structure.

17. The method according to claim 12, wherein the cyclic structure of at least one of $R^2$ and $R^3$ is an aromatic hydrocarbon group.

18. The method according to claim 12, wherein the cyclic structure of each of $R^2$ and $R^3$ is an aromatic hydrocarbon group.

19. The method according to claim 12, wherein the monovalent onium cation is a sulfonium cation or an iodonium cation.

20. The onium salt compound according to claim 11, wherein each of $R^2$ and $R^3$ is independently selected from the group consisting of structures,

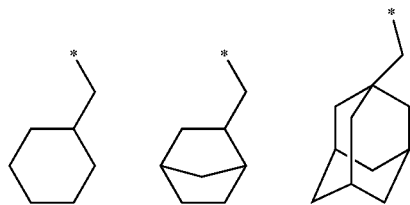

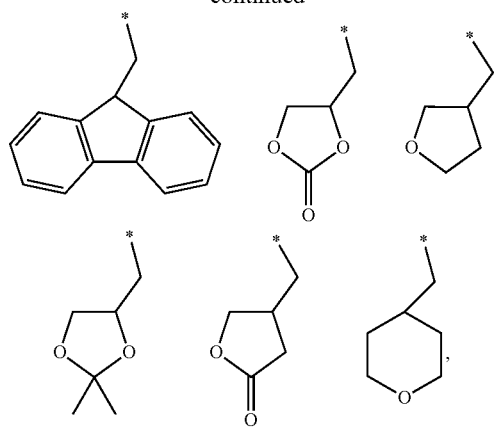

where each * is a hand bonding to $X^1$ or $X^2$.

* * * * *